US005569165A

United States Patent [19]

Chin et al.

[11] Patent Number: 5,569,165
[45] Date of Patent: Oct. 29, 1996

[54] APPARATUS FOR MECHANICAL ABDOMINAL WALL RETRACTION

[75] Inventors: Albert K. Chin, Palo Alto; Edmund K. M. Tsoi, San Francisco, both of Calif.

[73] Assignee: Origin Medsystems, Inc., Menlo Park, Calif.

[21] Appl. No.: 366,367

[22] Filed: Dec. 29, 1994

Related U.S. Application Data

[63] Continuation of Ser. No. 959,717, Oct. 13, 1992, abandoned, which is a continuation of Ser. No. 890,033, May 28, 1992, abandoned, which is a continuation-in-part of Ser. No. 706,781, May 29, 1991, abandoned.

[51] Int. Cl.$^6$ .................................................. A61B 17/02
[52] U.S. Cl. ........................ 600/204; 600/227; 294/81.3; 294/81.4
[58] Field of Search ..................... 600/204, 227, 600/234, 228, 231, 232, 233; 294/119.1, 81.3, 81.4, 81.5, 81.6; 606/198

[56] References Cited

U.S. PATENT DOCUMENTS

| | | | |
|---|---|---|---|
| 1,928,213 | 9/1933 | Showers et al. | 294/81.3 X |
| 2,604,352 | 7/1952 | Gonser | 294/119.1 X |
| 2,841,148 | 7/1958 | Kadavy . | |
| 3,561,810 | 2/1971 | Newsted | 294/81.3 |
| 3,572,803 | 3/1971 | Pompe | 294/81.3 |
| 3,655,232 | 4/1972 | Martelee | 294/119.1 X |
| 3,670,912 | 6/1972 | Dunbar | 294/119.1 X |
| 4,052,980 | 10/1977 | Grams et al. . | |
| 4,178,119 | 12/1979 | Busch | 294/119.1 X |
| 4,482,289 | 11/1984 | Inaba et al. | 414/736 |
| 4,510,926 | 4/1985 | Inaba | 600/234 X |
| 4,622,955 | 11/1986 | Fakhrai | 600/228 X |
| 4,705,040 | 11/1987 | Mueller et al. . | |
| 4,968,077 | 11/1990 | Redmon et al. | 294/119.1 X |
| 5,109,831 | 5/1992 | Forrest et al. | 600/228 |
| 5,152,279 | 10/1992 | Wilk | 128/17 |
| 5,163,949 | 11/1992 | Bonutti | 606/192 |
| 5,178,133 | 1/1993 | Pena | 128/20 |
| 5,235,966 | 8/1993 | Jamner | 128/20 |
| 5,280,782 | 1/1994 | Wilk | 128/20 |
| 5,293,863 | 3/1994 | Zhu et al. | 128/20 |
| 5,318,012 | 6/1994 | Wilk | 128/20 |
| 5,318,013 | 6/1994 | Wilk | 128/20 |
| 5,339,801 | 8/1994 | Poloyko et al. | 128/20 |
| 5,351,679 | 10/1994 | Mayzels et al. | 128/20 |

FOREIGN PATENT DOCUMENTS

| | | | |
|---|---|---|---|
| 464463A | 1/1992 | European Pat. Off. | A61B 17/28 |
| 1480384 | 5/1967 | France | 294/81.3 |
| 527273 | 4/1932 | Germany | 294/81.5 |
| 9102493 | 3/1991 | WIPO | A61B 17/22 |
| 9114392 | 10/1991 | WIPO | A61B 1/32 |

OTHER PUBLICATIONS

*Surgical Laparoscopy and Endoscopy*, vol. 1, No. 2, Jun. 27 1991, Raven Press Ltd., M. M. Gazayerli: "The gazayerli endoscopic retractor Model 1", pp. 98–100.

*Primary Examiner*—Michael H. Thaler
*Attorney, Agent, or Firm*—Limbach & Limbach L.L.P.

[57] ABSTRACT

An apparatus for allowing two retractors, preferably fan retractors, to be used to lift the abdominal wall to provide improved visualization and working space in the abdomen of obese patients, and in the lateral regions of the abdomen of normal patients. The apparatus connects a first retractor and a second retractor to a mechanical lifting arm, and comprises a bar, and first, second, and third connecting devices. The first and second connecting devices are each slidably mounted on the bar, are each lockable to the bar, and connect the first retractor and the second retractor, respectively, to the bar. The third connecting device is attached to the center of the bar and connects the bar to the mechanical lifting arm. The apparatus is used by making a first incision and a second incision in the abdominal wall at separated locations. The first retractor is inserted into the first incision, and the second retractor is inserted into the second incision. The first retractor and the second retractor are attached to the crossbar, and a lifting force is applied to the crossbar.

21 Claims, 13 Drawing Sheets

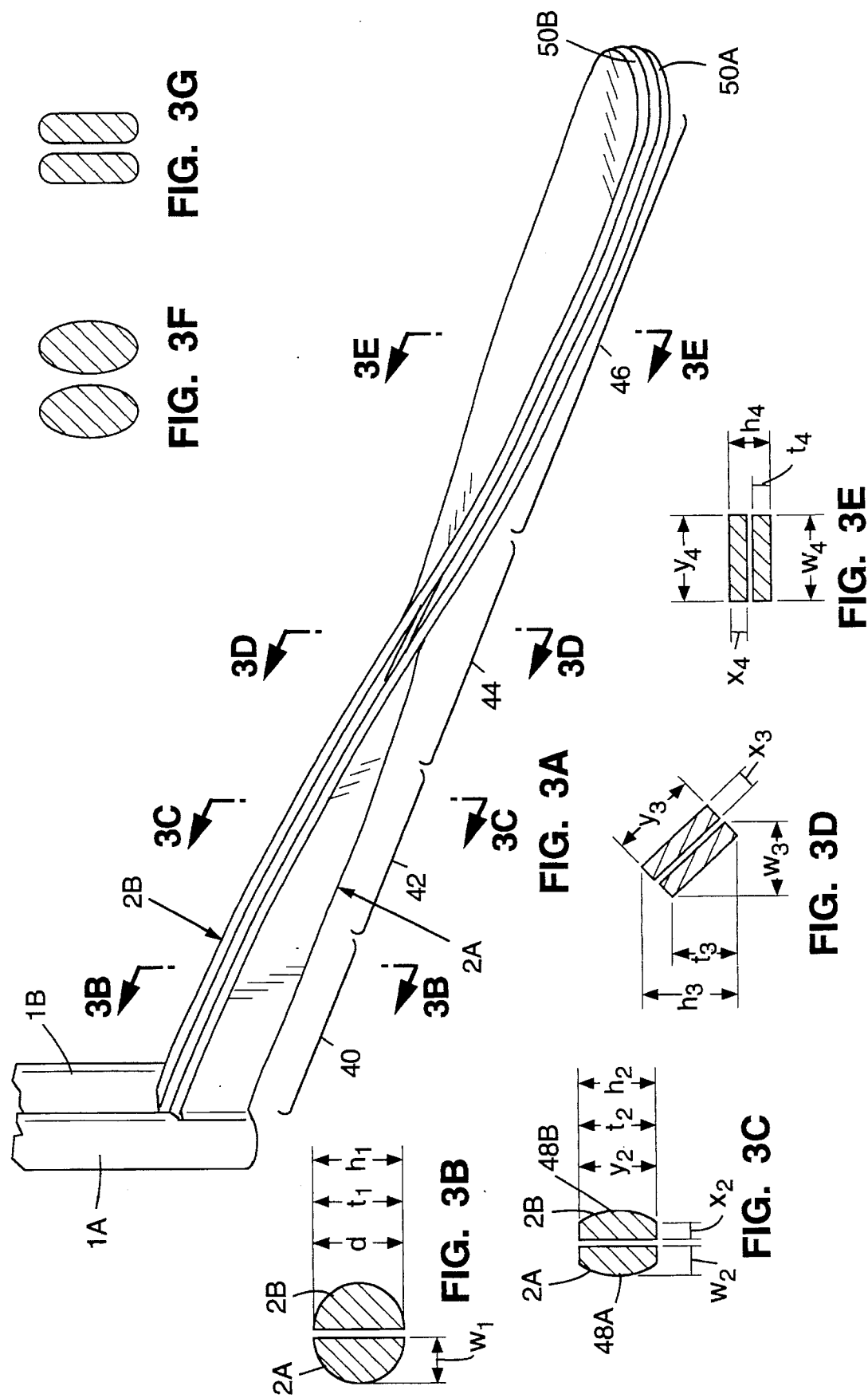

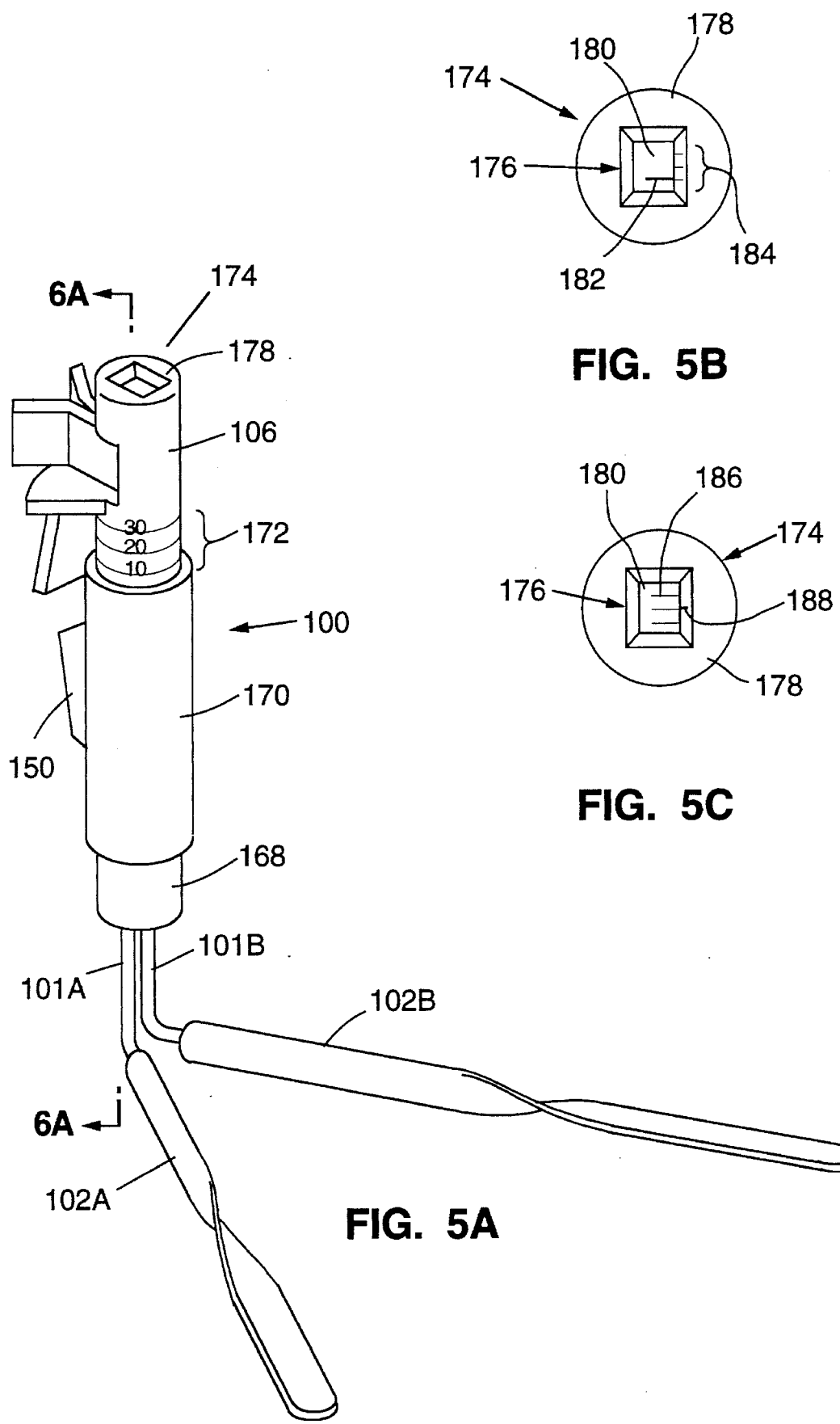

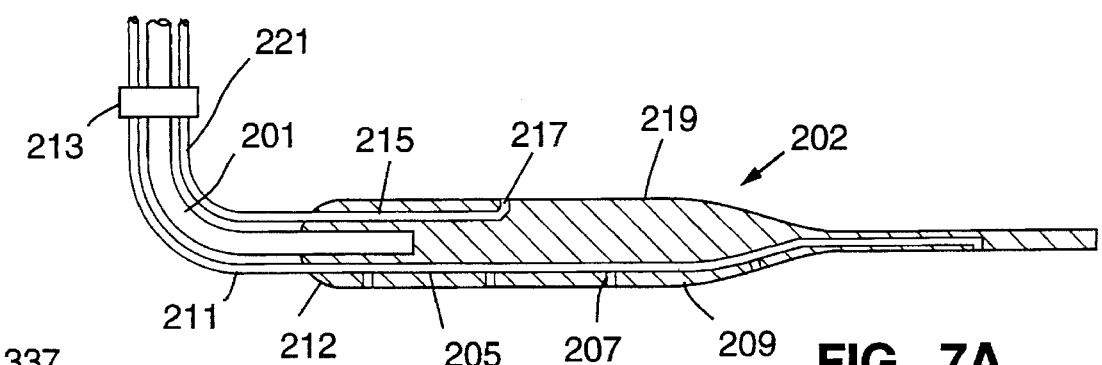
FIG. 7A
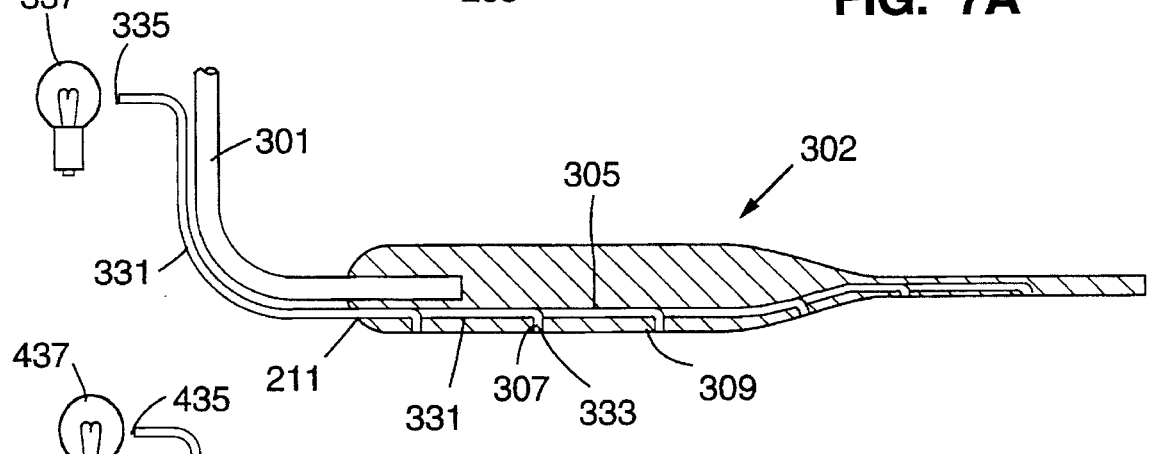
FIG. 7B
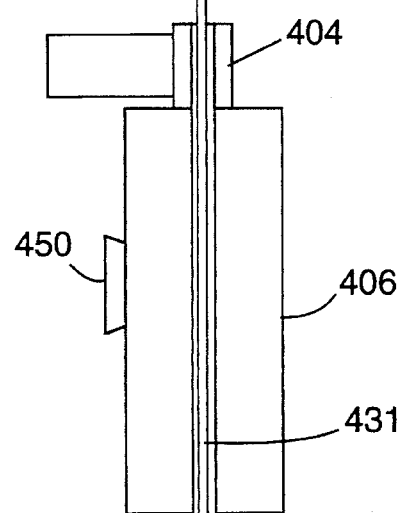
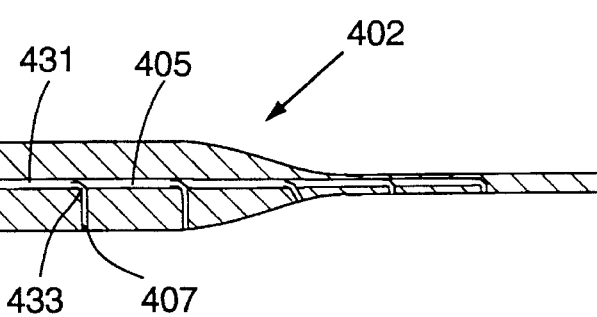
FIG. 7C

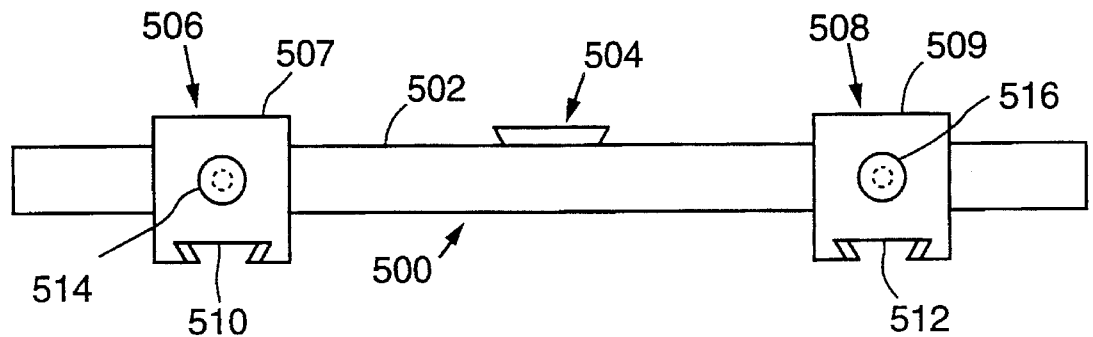
FIG. 9A
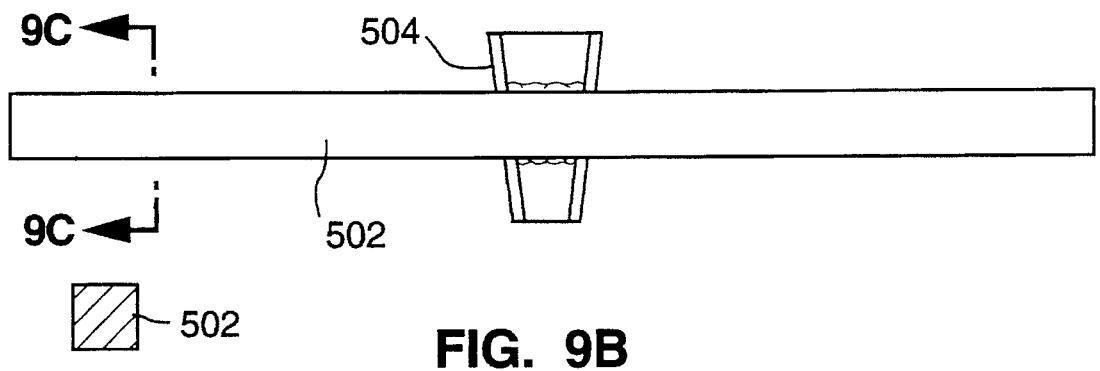
FIG. 9B
FIG. 9C
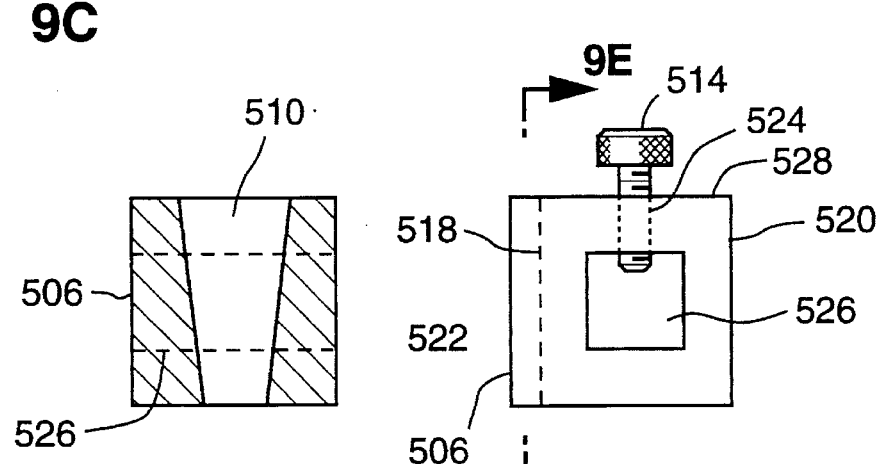
FIG. 9E
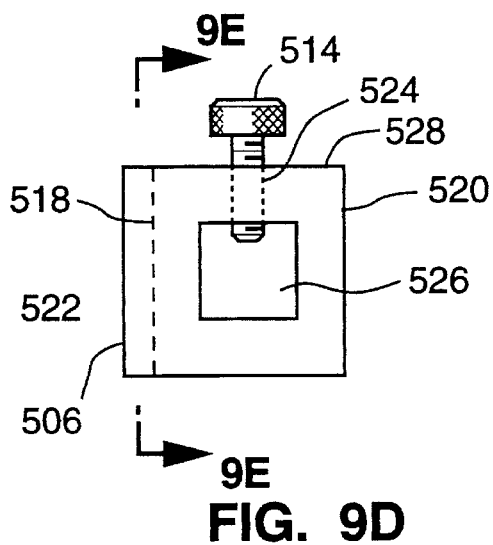
FIG. 9D

APPARATUS FOR MECHANICAL ABDOMINAL WALL RETRACTION

This is a continuation of application Ser. No. 07/959,717 filed on Oct. 13, 1992, now abandoned, which is a continuation of application Ser. No. 07/890,033 filed May 28, 1992, now abandoned, which is a continuation-in-part of application Ser. No. 07/706,781 filed on May 29, 1991, now abandoned.

BACKGROUND OF THE INVENTION

Laparoscopy dates back to the turn of the 20th Century. Early laparoscopic techniques were used primarily for diagnostic purposes to view the internal organs, without the necessity of conventional surgery. Since the 1930s, laparoscopy has been used for sterilization and, more recently, for suturing hernias. U.S. Pat. Nos. 4,919,152 and 4,944,443 are concerned with techniques for suturing hernias. Another recent innovation is the use of laparoscopic surgery for removing the gallbladder.

In the course of performing laparoscopic procedures in the abdomen, it is necessary to raise the abdominal wall to create space in which to work. A well-known method of raising the abdominal wall is to insufflate the abdominal cavity with a suitable insufflation gas, such as air, or carbon dioxide. A significant disadvantage of gas insufflation is that instruments must be passed into the abdominal cavity through gas-tight seals, which significantly reduce the surgeon's feel of the instruments.

Several mechanical alternatives to gas insufflation have been proposed. The Gazayerli Endoscopic Retractor Model 1, described in *SURGICAL LAPAROSCOPY AND ENDOSCOPY*, Vol. 1, No. 2, 1991, pages 98–100, has a rigid rod with a hinged blade at the distal end. The blade can rotate through 360 degrees about an axis perpendicular to the long axis of the rod. The blade is aligned with the long axis of the rod for insertion into the abdomen through a small puncture. Once inside the abdomen, the blade is swivelled through about 90 degrees to form a T-shaped structure. The proximal end of the rod can be raised by hand or by a rope, pulley and weight arrangement. Raising the rod causes the blade to engage the abdominal wall and to lift it.

French patent application no. 90-03980 shows a wire structure that is threaded into the abdomen through a small puncture to engage and to lift the abdominal wall. The application also shows a fan retractor that has a first angle-shaped member having a first leg that engages with the abdominal wall, a tubular second leg having a bore, and a third leg, remote from the first leg, that has a hook-shaped member on its end distal from the second leg. A second angle-shaped member has a first leg that engages with the abdominal wall, a second leg that pivots within the bore of the second leg of the first angle-shaped member, and a third leg, remote from the first leg, that serves as an operating lever for the second angle-shaped member. The first legs of the angle-shaped members are closed together to insert them into the abdominal cavity through an incision. The third leg of the second angle-shaped member is then operated to spread the first leg of the second angle-shaped member apart from the first leg of the first angle-shaped member. The first legs are engaged with the peritoneum inside the abdominal cavity. A lifting force is then applied to the hook-shaped member to lift the retractor and hence to lift the abdominal wall.

U.S. patent application Ser. No. 07/706,781, the application of which the parent of this application is a Continuation-in-Part, describes a number of different mechanical devices that are inserted through one or more punctures into the abdomen. All or part of the device is then lifted to lift the abdominal wall away from the underlying abdominal organs. One of the devices described in this application is a fan retractor that is inserted in a closed condition into the abdomen, spread apart once inside the abdomen, and brought into contact with the peritoneum inside the abdomen. The fan retractor is then raised by a lifting arm to lift the abdominal wall.

U.S. patent application Ser. No. 07/890,033, the application of which this application is a Continuation-in-Part, describes a fan retractor in which the second legs are adapted for insertion properitoneally, i.e., between the peritoneum and the properitoneal fat layer, by reducing their thickness and stiffness distally from the first legs. The peritoneum acts as a drape, and prevents the second legs from snagging and injuring the bowel or omentum. After the fan retractor has been placed between the peritoneum and the properitoneal fat layer, and its second legs have been spread apart, the fan retractor is raised by a lifting arm to lift the abdominal wall.

A single fan retractor raised by a lifting arm functions adequately in patients of normal body habitus and in mildly obese patients. It also functions adequately in procedures that involve manipulations and dissection of tissue and organs situated in the center of the abdomen. Inadequate visualization and working space occurs when a single fan retractor is used in obese and morbidly obese patients, and in procedures in normal patients where access to lateral regions of the abdomen, such as the paracolic gutters, is required.

OBJECTS AND SUMMARY OF THE INVENTION

In the following description, the word "organ" will be used to mean an organ or a tissue that is retracted by a retraction device. The word "treat" will be used to mean both treat and observe, and the word "treatment" will be used to mean both treatment and observation. The word "tissue" or the phrase "tissue to be treated" will both be used to mean the organ or the tissue that is treated after the abdominal wall has been retracted.

It is an object of the present invention to provide an apparatus for mechanically retracting the abdominal wall to provide a generous amount of visualization and working space in obese and morbidly obese patients, and in the lateral regions of the abdomen of normal patients. It is also an object of the invention to provide a method for mechanically retracting the abdominal wall of obese and morbidly obese patients to provide adequate visualization and working space.

The invention provides an apparatus for connecting a first retractor and a second retractor to a mechanical lifting arm to raise the abdominal wall. The apparatus includes a bar, and first, second, and third connecting devices. The first connecting device is slidably mounted on the bar, is lockable to the bar, and connects the first retractor to the bar. The second connecting device is slidably mounted on the bar, is lockable to the bar, and connects the second retractor to the bar. The third connecting device is attached to the center of the bar and connects the bar to the mechanical lifting arm.

The first and second connecting devices preferably each include a body having a hole passing through it for receiving the bar, a connector attached to the body to which a fan retractor can be connected, and a device for locking the body to the bar.

The apparatus also preferably includes a device for disposing the first and second connecting devices symmetrically about the third connecting device.

In the method for lifting the abdominal wall according to the invention, a first retractor, a second retractor, and a crossbar are provided. A first incision and a second incision are made in the abdominal wall at separated locations. The first retractor is inserted into the first incision, and the second retractor is inserted into the second incision. The first retractor and the second retractor are attached to the crossbar, and a lifting force is applied to the crossbar.

The method according to the invention is preferably practiced using two fan retractors used properitoneally, but the method may also be carried out using angle-shaped hook retractors or other types of retractors. The retractor may also be used abdominally.

BRIEF DESCRIPTION OF THE DRAWINGS

FIG. 3A is a perspective view of the preferred embodiment of the second legs of a properitoneal fan retractor in their closed position.

FIG. 3B is a cross sectional view of the first part of the second legs of a properitoneal fan retractor, taken on the line A–A' in FIG. 3A.

FIG. 3C is a cross sectional view of the second part of the second legs of a properitoneal fan retractor, taken on the line B–B' in FIG. 3A.

FIG. 3D is a cross sectional view of the third part of the second legs of a properitoneal fan retractor, taken on the line C–C' in FIG. 3A.

FIG. 3E is a cross sectional view of the fourth part of the second legs of a properitoneal fan retractor, taken on the line D–D' in FIG. 3A.

FIG. 3F is a cross sectional view of the first part of an alternative embodiment of the second legs of a properitoneal fan retractor, in which the first part of the second legs has an oval cross-section.

FIG. 3G is a cross sectional view of the second part of an alternative embodiment of the second legs of a properitoneal fan retractor, in which the first part of the second legs has an oval cross-section.

FIG. 5A is a perspective view of a preferred embodiment of a properitoneal fan retractor.

FIG. 5B is a plan view of a first embodiment of the additional lifting force indicator of a properitoneal fan retractor.

FIG. 5C is a plan view of a second embodiment of the additional lifting force indicator of a properitoneal fan retractor.

FIG. 7A is a longitudinal cross sectional view of a second leg of a properitoneal fan retractor. The second leg has an internal bore arrangement providing aspiration and/or irrigation.

FIG. 7B is a longitudinal cross sectional view of a second leg of a properitoneal fan retractor. The second leg has an internal bore arrangement providing working lighting using optical fibres.

FIG. 7C is a longitudinal cross sectional view of a second leg of a properitoneal fan retractor. The second leg has an internal bore arrangement providing working lighting using optical fibres brought into the second leg through a bore in the first leg.

FIG. 8A is a longitudinal cross section of the abdomen, showing the abdominal wall, the peritoneum, and the fan retractor correctly positioned adjacent to the abdominal wall prior to opening the second legs of the retractor.

FIG. 8B is a plan view of the abdomen showing the fan retractor correctly positioned relative to the center line of the abdomen, prior to opening the second legs of the retractor.

FIG. 8C is a plan view of the abdomen showing the fan retractor symmetrically positioned relative to the center line of the abdomen after the second legs of the retractor have been opened.

FIG. 8D is a longitudinal cross section of the abdomen after the abdominal wall has been lifted by the fan retractor connected to a lifting bar, showing the abdominal wall, the peritoneum, and the fan retractor with the distal parts of its second legs bent to conform with the lifted shape of the anterior abdominal wall.

FIGS. 9A through 9E show a crossbar according to the invention, wherein:

FIG. 9A shows a plan view;

FIG. 9B shows an elevation of the bar with the arm connector attached;

FIG. 9C shows a cross section of the bar on the line XX' in FIG. 9B;

FIG. 9D shows a side view of one of the retractor mounts; and

FIG. 9E shows a cross section of one of the retractor mounts on the line YY' in FIG. 9D.

FIGS. 10A through 10D show a number of arrangements for locating the retractor mounts on bar symmetrically about the lifting arm connector, wherein FIG. 10A shows distance marks on the bar;

FIG. 10B shows a rack and pinion arrangement;

FIG. 10C shows a cord and pulley arrangement; and

FIG. 10D shows a lead screw arrangement.

FIGS. 11A through 11F illustrate the method according to the invention of mechanically raising the abdominal wall using two retractors and a crossbar according to the invention, wherein FIG. 11A is a lateral cross section of the abdomen showing a first fan retractor being inserted into a first incision at the umbilicus;

FIG. 11B is a lateral cross section of the abdomen showing the first fan retractor fully inserted between the peritoneum and the properitoneal fat layer;

FIG. 11C is a plan view of the abdomen showing the first fan retractor fully inserted with its second legs in their open position;

FIG. 11D is a plan view of the abdomen showing the first fan retractor fully inserted with its second legs in their open position and a second fan retractor inserted into a second incision at the epigastric point. The second legs of the second fan retractor have been advanced between the properitoneal fat layer and the peritoneum and are in their open position;

FIG. 11E is a plan view of the abdomen showing the first and second fan retractors attached to the crossbar; and FIG. 11F is a plan view of the abdomen showing the first and second fan retractors attached to the crossbar, and the crossbar attached to a lifting arm mounted on the operating table.

DETAILED DESCRIPTION OF THE INVENTION

Figure 1:
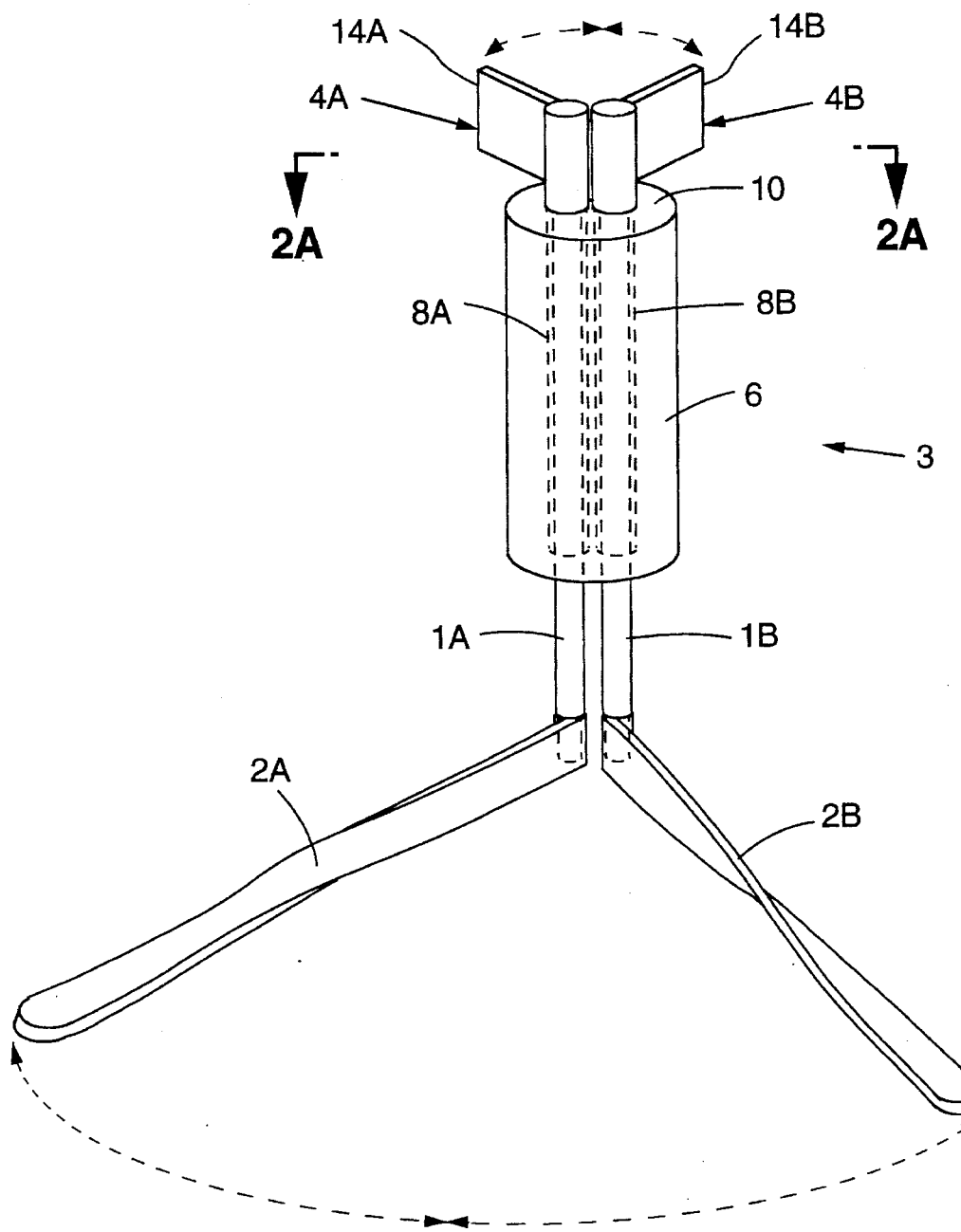
FIG. 1 is a perspective view of a simplified version of a fan retractor for properitoneal use.

A number of properitoneal fan retractors that are preferably used to practice the method of the invention and that can be used in connection with the apparatus of the invention will first be described. A simplified representation of a properitoneal fan retractor is shown in FIG. 1. The fan retractor 3 has a pair of first legs 1A and 1B, including the leg actuators 4A and 4B, a pair of second legs 2A and 2B, and a mounting block 6 to which the lifting force is applied. The second legs are shown schematically: their specific shape will be described in detail below in connection with FIGS. 3A through 3G.

The mounting block 6 is cylindrical and includes two axial bores 8A and 8B, symmetrically offset from the axis, that receive the first legs 1A and 1B, respectively. The diameter of the bores is such that the bores snugly receive the first legs with the first legs free to rotate within their respective bores. The mounting block 6 is preferably moulded from a suitable plastic, such as polycarbonate, but other materials, such as stainless steel, can be used.

The first legs 1A and 1B are substantially straight, cylindrical metal rods. In the preferred embodiment, they are made from stainless steel and are about 4.5" long and about 0.15" in diameter.

The leg actuators 4A and 4B are attached to the end of the first legs 1A and 1B, respectively, remote from the second legs, on the opposite side of the first legs from the second legs. The leg actuators bear against the upper face 10 of the mounting block 6 and transfer the lifting force from the upper face 10 of the mounting block 6 to the first legs. The leg actuators are attached to the first legs so that they can withstand a force of several tens of kilograms exerted in the direction of the first legs.

The leg actuators 4A and 4B rotate the first legs. This changes the angular positions of the second legs 2A and 2B with respect to one another. The second legs 2A and 2B are preferably incapable of independent movement. If one of the second legs, for example 2A, is moved by the operating lever 14A of the leg actuator 4A through a certain angle, the other of the second legs, for example 2B, moves through substantially the same angle in the opposite direction.

Preferably, the operating levers 14A and 14B of the leg actuators are on the opposite side of the first legs from the second legs. Moving the operating levers 14A and 14B of the actuators 4A and 4B away from one another brings the second legs towards being parallel to one another (closed position), and bringing the operating levers together splays the second legs apart (open position). This mode of operating is preferred, especially for properitoneal use, since the second legs can be opened, and the peritoneum detached from the properitoneal fat layer, simply by squeezing the operating levers together. However, the operating levers may be mounted on the same side of the first legs as the second legs, if desired. Mounted in this way, the operating levers operate in the opposite sense, i.e., squeezing the operating levers together closes the second legs.

Figure 2A:
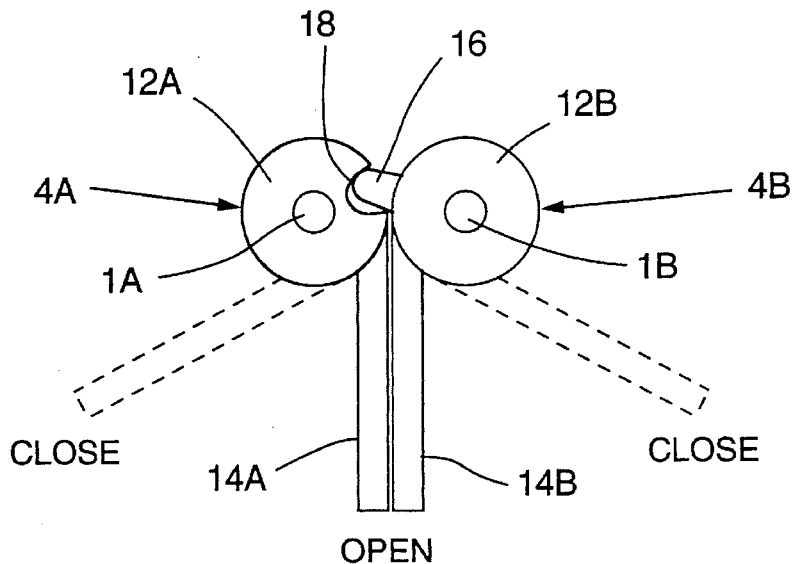
FIG. 2A is a cross sectional view of the leg actuators of a properitoneal fan retractor, taken along the line X–X' in FIG. 1.

The leg actuators 4A and 4B are linked to cause the second legs to move equally and oppositely. Any rotation of one of the leg actuators causes an equal and opposite rotation in the other of the leg actuators. Many known mechanisms exist for providing such relative motion. A cross section of the leg actuators of the preferred embodiment is shown in FIG. 2A. The leg actuators 4A and 4B each comprise a bush 12A, 12B mounted on the respective first leg 1A, 1B, and an operating lever 14A, 14B. The operating levers 14A and 14B translate a lateral movement of the operator's thumb or finger into a rotation of the respective leg actuator 4A and 4B, and of the respective first leg 1A and 1B.

The bush 12B is provided with a peg 16 that engages with a socket 18 provided in the other bush 12A. The respective locations of the peg and the socket can be interchanged if desired. The peg and socket arrangement responds to the rotation of either one of the leg actuators 4A and 4B, and imparts an equal and opposite rotation on the other. This arrangement ensures that the second legs 2A and 2B open symmetrically and reduces the risk of one of the second legs inadvertently abutting against, and possibly penetrating, the abdominal wall. This is particularly desirable when the retractor is used properitoneally and the positions of the second legs cannot be seen directly.

Instead of the peg and socket arrangement shown, teeth can be moulded in the outer surfaces of the leg actuators 4A and 4B. Alternatively, the leg actuators can be clamped together in the direction perpendicular to the first legs 1A and 1B, and the resulting friction between them used impart the desired relative motion. Providing one or both of the leg actuators with a high friction surface is desirable in such an arrangement. As a further alternative, the rotation of the first legs themselves can be linked, instead of linking the rotation of the leg actuators.

Figure 2B:
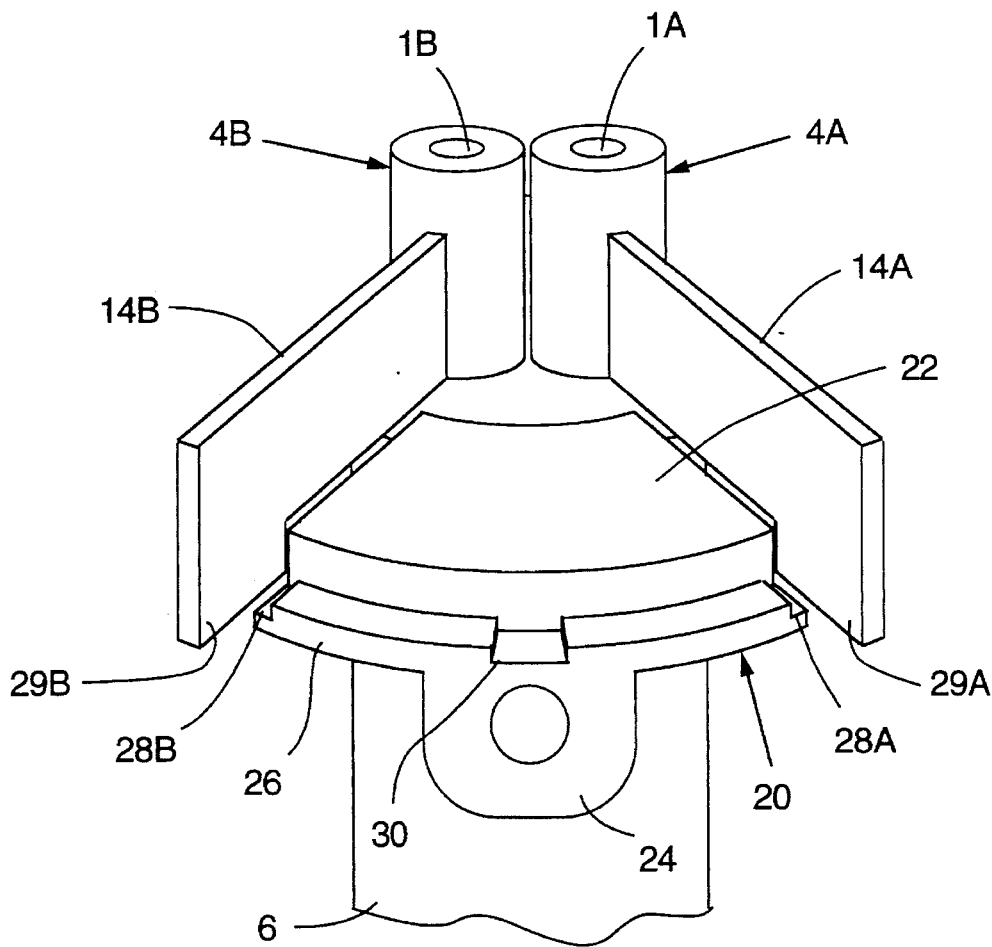
FIG. 2B is a perspective view of the leg actuators of a properitoneal fan retractor.

FIG. 2B shows details of the locking mechanism that holds the operating levers 14A and 14B in their open or closed positions, and hence holds the second legs 2A and 2B in their closed or open positions respectively. The sector 20 is mounted on the mounting block 6 adjacent to the operating levers 14A and 14B. In the preferred embodiment, the sector is moulded integrally with the mounting block. Relative to the operating levers 14A and 14B, the sector is slightly concave, and the operating levers 14A and 14B are biassed against the face 22 of the sector. This causes the sector to apply a frictional force to the operating levers. The frictional force holds the operating levers in any position in which they are set.

The frictional force can be released by pressing the button 24 towards the mounting block 6. The button is attached to, and preferably forms an integral part of, the sector 20. Pressing the button towards the mounting block bends the sector out of contact with the operating levers 14A and 14B, which releases the frictional force.

The skirt 26 of the sector 20 may additionally or alternatively be provided with one, two, or all of the notches 28A, 28B and 30, and the operating levers 14A and 15B provided with the operating lever extensions 29A and 29B. The notches 28A and 28B engage with the operating lever extensions 29A and 29B, respectively, when the operating levers are in the open position, i.e., when the second legs are in their closed position. The notches 28A and 28B lock the operating levers in position, and positively hold the second legs in their closed position. Because the motions of the leg actuators 4A and 4B are linked, one of the notches 28A and 28B may be omitted, if desired.

The notch 30 engages with the operating lever extensions 29A and 29B when the operating levers are in their closed position, i.e., when the second legs are in their open position. The notch 30 locks the operating levers in position, and positively holds the second legs in their open position.

If the notches 28A, 28B and 30 are provided, a clearance must be provided between the sector 20 and the operating levers 14A and 14B to enable the notches to engage with the operating lever extensions 29A and 29B. However, with this arrangement, the skirt 26 applies a frictional force against to the operating lever extensions capable of holding the operating levers, and hence the second legs, in intermediate positions.

FIG. 3A shows a perspective view of the second legs 2A and 2B of a properitoneal fan retractor. FIGS. 3B through 3E show cross sections views of the second legs at various points along their lengths. For both properitoneal use and for conventional use, the stiffness of the second legs in the lifting direction, i.e., in the direction of the first legs, is required to decrease distally from the first legs. Distally reducing the stiffness of the second legs enables the second legs to bend to conform to the shape of the raised abdomen while having sufficient strength to provide the lifting force necessary. This spreads the lifting force evenly along the length of the second legs, instead of concentrating the lifting force towards their distal ends.

For properitoneal use, second legs that are relatively flat are desirable to make it easy to insert the legs between the peritoneum and the properitoneal fat layer. Flat legs, i.e., legs that are thin over all of their length, lack sufficient strength to exert the required lifting forces of several tens of kilograms. Second legs having an effective thickness that decreases and an effective width that increases distally from the first legs are both easy to insert under the peritoneum and are strong enough to exert the required lifting forces. The increasing thickness of the second legs towards the first legs acts as a wedge to detach the peritoneum progressively from the properitoneal fat layer as the second legs are advanced under the peritoneum. The distally reducing thickness of the second legs also causes the stiffness of the second legs to reduce distally, which is desirable to enable the second legs to conform with the shape of the raised abdomen. The distally increasing width of the second legs helps maintain a more constant pressure against the peritoneum along the length of the second legs.

It is also desirable that the second legs form a relatively compact shape when in their closed position to reduce the size of the incision required to introduce the second legs into the abdomen, either conventionally or properitoneally.

The preferred design for the second legs that meets the requirements just stated is shown in FIGS. 3A through 3E. Both the cross sectional area and the cross sectional shape of the second legs change distally from the first legs 1A and 1B.

The preferred second legs can be regarded as having four distinct parts. In the first part 40 of the second legs, close to the first legs, the cross section of each second leg is substantially semi-circular, as shown in FIG. 3B. In the first part of the second legs, the second legs have an appreciable thickness $t_1$ in the direction of the first legs. This provides considerable beam strength and stiffness, measured in the direction of the first legs, so that the required retraction force can be exerted. The semicircular cross section enables the two second legs to fit together to form a compact shape when the retractor is in its closed position.

In the second part 42 of the second legs, the thickness $t_2$ of the second legs 2A and 2B remains the same as the thickness $t_1$ of the first part 40, but the width $w_2$ of the second legs progressively reduces as the cross section changes from semi-circular to rectangular. FIG. 3C shows the cross section of the second legs towards the distal end of the second part where the outer surfaces 48A and 48B of the second legs are still slightly curved. At the distal end of the second part, the outer surfaces 48A and 48B are substantially straight. The length $y_2$ of the major axis of the rectangular cross section is substantially equal to the diameter d of the semicircular cross section of the first part 40 of the second legs, shown in FIG. 3B.

In the second part 42, the second legs have an appreciable thickness $t_2$ in the direction of the first legs. The beam strength and stiffness of the second legs, although appreciable, is less than in the first part 40 because the width $w_2$ of the second part is less than the width $w_1$ of the first part. The rectangular cross section enables the second parts of the second legs to fit together to form a compact shape when the retractor is in its closed position, as shown in FIG. 3C.

In the third part 44 of the second legs, the second legs have the same rectangular cross section as the distal part of the second part 42, but the second leg is twisted progressively through about 90 degrees over the length of the third part. The cross section of the legs about half-way along the third part, at which point the legs are twisted through about 45 degrees, is shown in FIG. 3D. The dimensions, $x_3$ and $y_3$ of the minor and major axes, respectively, of the rectangular cross section remain the same as the dimensions $x_2$ and $y_2$ of the minor and major axes, respectively, of the rectangular cross section in the second part. Along the third part distally from the second part, the twisting the second legs causes the effective thickness $t_3$ of the leg to decrease and the effective width $w_3$ of the leg to increase.

Both of the second legs are twisted in the same direction through the same angle so that they will fit together to form a compact shape when the retractor is in its closed position. The two second legs are not identically twisted, however. So that the fourth part 46 of one of the second legs can fit on top of the fourth part of the other of the second legs when the retractor is in its closed position, the twist in one of the second legs is slightly offset in the direction of the first legs, and the twist in the other of the second legs is offset in the direction opposite to the direction of the first legs. Alternatively, the second legs can be made with identical twists, and be mounted on the first legs so that one forms an angle of slightly more than 90 degrees with its first leg, and the other forms an angle of slightly less than 90 degrees with its first leg.

In the third part 44, the second legs have an effective thickness $t_3$ in the direction of the first legs that progressively decreases distally from the first legs. Hence, the beam strength and stiffness of the second legs also decrease distally from the first legs. Finally, the insertion height $h_3$ of the second legs when the retractor is in its closed position progressively decreases distally from the first legs.

In the fourth part 46 of the second legs, the second legs have the same rectangular cross section as the distal part of the second part 42, but the cross section is substantially perpendicular to the cross section of the second part, as shown in FIG. 3E. The dimensions $x_4$ and $y_4$ of the minor and major axes, respectively, of the rectangular cross section remain the same as the dimensions $x_2$ and $y_2$ of the minor and major axes, respectively, of the rectangular cross section in the second part.

In the fourth part 46, the second legs have an effective thickness $t_1$ in the direction of the first legs that remains substantially constant and equal to the physical thickness $y_4$ of the second legs. Hence, the beam strength and stiffness of the second legs are also substantially constant in the fourth part, and are considerably less than in the first and second parts, and in the part of the third part proximal to the first legs. The effective width $w_4$ of the second legs in the fourth part is substantially equal to the physical width $x_4$ of the legs, and is considerably greater than in the first and second parts. This considerably reduces the pressure that the fourth parts of the second legs of the retractor exert per square centimeter of abdominal wall. Finally, the insertion height $h_4$ of the fourth part of the second legs when the retractor is in its closed position is substantially equal to twice the physical thickness $y_4$ of the second legs as a result of the fourth parts of the second legs stacking on top of one another. This dimension is relatively small and makes it easy to insert distal ends of the second legs of the retractor between the peritoneum and the peritoneal fat layer. Also, the distal ends 49A and 49B of the second legs are rounded to further ease insertion.

The four parts of the second leg are preferably approximately equal to one another in length. However, the relative lengths of the four parts can be varied to achieve a better stiffness versus distance from the first legs characteristic.

The first part 40 of the second legs preferably has a semicircular cross section. An alternative oval cross section is shown in FIG. 3F, with the corresponding cross section of the second part 42 shown in FIG. 3G. The cross sections of the third and fourth parts are substantially the same as the cross sections of the third and fourth parts shown in FIGS. 3D and 3E, respectively.

Second leg blanks having the required thickness profile for the preferred embodiment, but lacking a twisted third part 44, can be molded using a relatively simple mold. From the second leg blanks, second legs with the flat side of the first part on the left, like second leg 2A, and second legs with the flat side of the first part on the right, like second leg 2B, can be made. After a second leg blank has been moulded, it is placed in a twisting jig and supported at the distal end of its second part 42. The fourth part 46 is clamped in a rotating port of the jig. The third part of the leg is heated to soften it, and the rotating part of the jig is rotated through about 90 degrees to impart the desired twist in the third part 44 of the leg. The leg is left to cool before it is removed from the jig. The orientation of the flat side of the first part of the leg in the twisting jig determines whether a type-2A leg or a type-2B leg is made. The twisting direction is the same for both types of leg.

Preferably, a more complex tool is made, and the second legs are molded the required twist. With considerably more complex tools, second legs can be made having a stiffness versus distance from the first legs characteristic that is fully optimized along the length of the leg for its intended application.

Figure 4A:
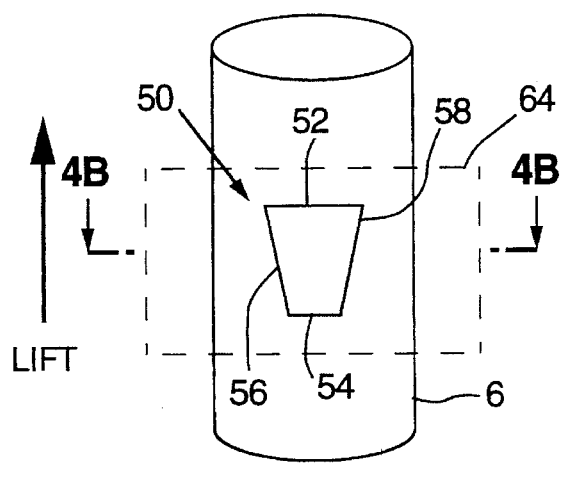
FIG. 4A is a perspective view of the mounting block and lifting bar adaptor of a simplified properitoneal fan retractor.
Figure 4B:
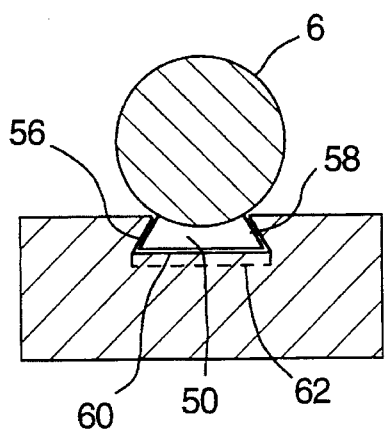
FIG. 4B is a cross sectional view of the mounting block and lifting bar adaptor of a simplified properitoneal fan retractor.

The mounting block 6 can be provided with a variety of attachments suitable for coupling to known lifting arms. In the preferred embodiment, the mounting block is provided with a dovetail connector 50, as shown in FIGS. 4A and 4B. The dovetail connector is trapezoidal, with its parallel sides 52 and 54 perpendicular to the lifting direction, and its long parallel side 52 spaced from its short parallel side 54 in the lifting direction. The non-parallel sides, 56 and 58, form an acute angle with the front face 60. The arrangement of non-parallel sides forming an acute angle with the front face forms a positive lock with a dovetail slot 62, which is a female version of the dovetail connector 50, formed in the lifting arm adaptor 64. The lifting arm adaptor is attached to the lifting arm by conventional means (not shown).

The male dovetail connector 50 and female dovetail connector 62 together form a dovetail connector that is a unidirectional lifting force coupling. The dovetail connector will transmit to the mounting block 6 a lifting force applied to the lifting arm adaptor 64 in the direction indicated by the arrow 66. A force applied in the direction opposite to that shown by the arrow 66 causes the dovetail connector to disconnect, which prevents the coupling from transmitting any force in the opposite direction.

When the retractor is used for lifting, the retractor is inserted into the abdomen and the male dovetail connector 50 is mated with the female dovetail connector 62 in the lifting arm adaptor 64. The lifting arm is then raised to lift the abdominal wall, and is maintained in position during treatment. After treatment has been completed, the lifting arm is progressively lowered to return the abdominal wall to its normal position. At a point at which the direction of the lifting force applied to the dovetail connector reverses, the dovetail connector automatically disconnects. This prevents the reverse force from being transmitted to the retractor, and indicates to the operator that the lifting arm has been lowered far enough. The dovetail connector provides a safety mechanism that prevents compression injury to the bowel if the lifting arm is lowered too far.

FIG. 5A is a perspective view of a preferred form of a properitoneal fan retractor 100. In this preferred form, the first legs 101A and 101B are extended by about 1" (25 mm) distally from the leg actuators 104A and 104B. The extended parts of the first legs are bent through about 90 degrees. The part of each of the first legs distal from the bend is inserted into an axial bore in the first part of the respective second leg. This arrangement is stronger than the arrangement shown in FIG. 1.

Also, in the preferred form, the first legs 101A and 101B pass through offset axial bores in the cylindrical lower mounting block 168, which is slidably mounted in the lower part of the bore of the mounting sleeve 170. The main mounting block 106 is spring mounted in the upper part of the bore of the mounting sleeve 170, as will be described in connection with FIG. 6A below. The dovetail connector 150 is mounted on the mounting sleeve 170, instead of directly on the main mounting block 106. The main mounting block can rotate relative to the mounting sleeve and the male dovetail connector. This enables the second legs to face in any direction relative to the lifting arm prior to lifting. Once lifted, the lifting force prevents the main mounting block from rotating relative to the mounting sleeve, and holds the legs in the position in which they were set prior to lifting.

When the preferred embodiment of the retractor is used to retract the abdominal wall, the lifting force is applied to the mounting sleeve 170 through the male dovetail connector 150. The spring mounting of the main mounting block 106 enables the relative axial positions of the mounting sleeve and main mounting block to change in response to the lifting force. The mounting sleeve moves relative to the scale 172 marked on the cylindrical surface of the main mounting block, which indicates the magnitude of the lifting force. The lifting force indicator thus provided enables the lifting force to be monitored during the lifting process, and reduces the risk that an excessive lifting force will be used.

Alternatively, the lifting force scale (not shown) can be marked on the surface of the mounting sleeve 170 and a pointer (not shown) attached to the main mounting block 106 can move against the scale to indicate the lifting force.

The lifting force scale on the cylindrical surface of the mounting sleeve 170 or of the main mounting block 106 is most easily seen from the side. The preferred embodiment includes an additional lifting force indicator 174 on the end face 178 of the main mounting block to enable the lifting force to be monitored easily looking from above. The additional lifting force indicator is shown in detail in FIGS. 5B and 5C. The additional lifting force indicator includes a window 176 in the end face 178 of the main mounting block. A tape 180 moves in the window 176 in response to the motion of the main mounting block relative to the mounting sleeve as a result of the lifting force. In the variation shown in FIG. 5B, the tape is marked with a reference mark 182 that moves against the scale 184 marked in the window 176, adjacent to the tape 180. In the variation shown in FIG. 5C, the tape is marked with the scale 186 that moves against the reference mark 188 marked in the window 176, adjacent to the tape.

Figure 6A:
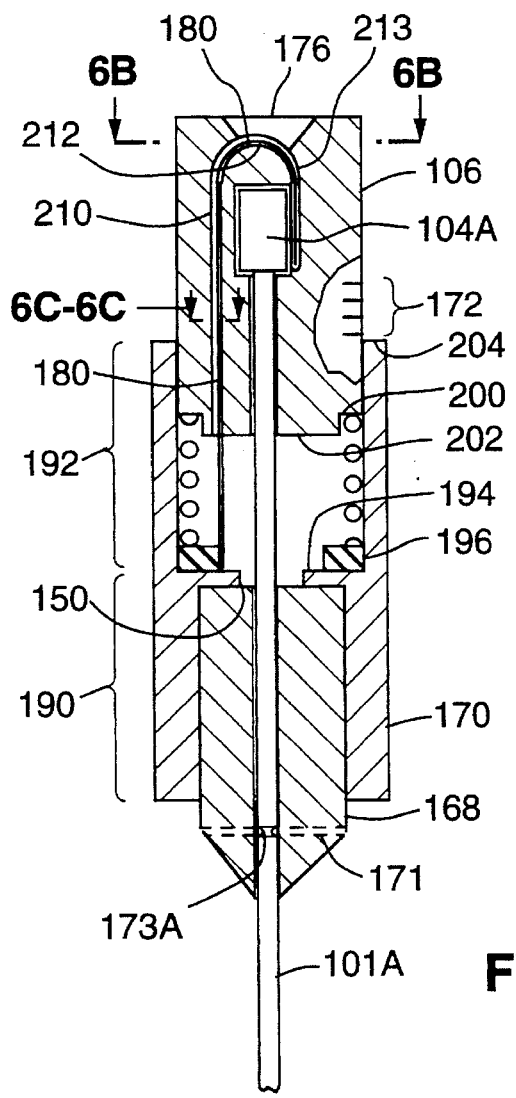
FIG. 6A is a cross sectional view of the preferred embodiment of a properitoneal fan retractor, taken along the line Z–Z' in FIG. 5A.

The assembly of the main mounting block 106, the lower mounting block 168, and the mounting sleeve 170, and details of the additional lifting force indicator are shown in FIG. 6A. The mounting sleeve 170 is a tubular piece of plastic or metal having a bore. The lower part 190 of the bore receives the lower mounting block 168. A pin 171 passes through a radial bore in the lower mounting block between the first legs, and engages with a groove in each of the first legs to axially locate the lower mounting block relative to the first legs. In FIG. 6A, the groove 173A in the first leg 101A is shown.

The upper part 192 of the bore, which preferably has a larger diameter than the lower part 190, receives the main mounting block 106. Separating the upper and lower parts of the bore is the lip 194, which provides an end-stop for upward movement of the lower mounting block 168 in the mounting sleeve 170. The lip 194 also supports the nylon washer 196 on which the lower end of the coil spring 198 rests. The lower surface 202 of the main mounting block 106 rests on the upper end of the coil spring 198, with a circumferential groove 200 in the lower surface receiving the spring.

A lifting force applied to the male dovetail connector 150 on the mounting sleeve 170 is transferred through the lip 194, the nylon washer 196, and the coil spring 198 to the main mounting block 106, and thence to the first and second legs of the retractor. Compression of the spring 198 in response to the lifting force allows the main mounting block 106 to move relative to the mounting sleeve 170, and causes the top rim 204 of the mounting sleeve to juxtapose a different point on the scale 172, which indicates the lifting force.

The main mounting block 106 includes an upper lifting force indicator passage 210 machined or moulded into it. The passage 210 has an exit in the lower face 202 of the main mounting block, and continues distally from the lower face in a substantially straight line parallel to the curved side of the main mounting block. Proximate to the window 176, the passage has a curved portion 212 that curves to form an arc in the window, followed by a straight portion 213 that returns at least part-way back towards the lower face 202.

The tape 180 runs through the passage 210. One end of the tape is attached to the mounting sleeve 170, preferably adjacent to the lip 194. The straight part of the passage 210 preferably has a cross section that curves across the width of the tape, as shown in FIG. 6C, to impart a stiffness to the tape.

Figures 6B, 6C:
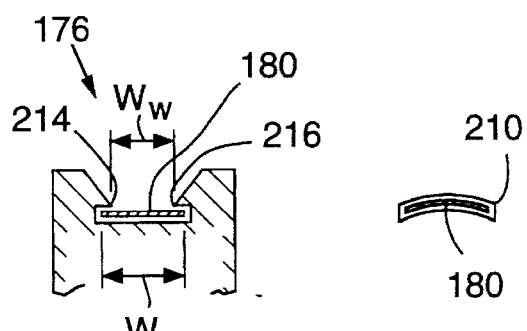
FIG. 6B is a cross sectional view of the additional lifting force indicating window of a properitoneal fan retractor, taken along the line P–P' in FIG. 6A.
FIG. 6C is a cross sectional view of the indicating tape channel of a properitoneal fan retractor, taken along the line Q–Q' in FIG. 6A.

The window 176 has a width $w_w$ that is narrower than the width $w_t$ of the tape 180, as shown in FIG. 6B. This enables the lips 214 and 216 to guide the tape in the curved part 212, where part of the wall of the passage is missing because of the window 176.

Compression of the spring 198 in response to the lifting force allows the main mounting block 106 to move relative to the mounting sleeve 170. This causes the tape 180 to move relative to the passage 210, and the reference mark 182 (or graduations 186) on the tape to move relative to the graduations 184 (or reference mark 188) in the window 176. The movement of the tape relative to the window indicates the lifting force.

Solid second legs are shown in FIG. 3A. The second legs may alternatively be provided with an arrangement of one or more internal passages, such as the arrangement of a longitudinal passage connecting to one or more transverse passages connecting to the surface of the leg shown in FIGS. 7A–7C. An internal passage can be dedicated to a specific purpose, or can be made to receive a variety of inserts that are plugged into the internal passage to provide different capabilities, as required.

FIGS. 7A and 7B show two examples of internal passage arrangements in which connections are made to an internal passage at the end of the second leg proximal to the first leg. Second legs can be also made with different internal passage arrangements, including, for example, arrangements with more or fewer longitudinal passages, with more or fewer transverse passages, and/or with transverse passages connecting to the side surfaces of the second legs.

FIG. 7A shows a second leg 202 attached to a first leg 201. The second leg 202 has an internal passage arrangement with two longitudinal passages 205 and 215. The longitudinal passage 205 is connected to a plurality of transverse passages, including the transverse passage 207, connecting to the lower surface 209 of the second leg. A pipe 211 is plugged into the proximal end 212 of the second leg to connect to the longitudinal passage 205. The pipe 211 is run up the outside of the first leg 201 to a suitable connection (not shown). The pipe 211 is retained in position relative to the first leg 201 by the clamp 213.

The longitudinal passage 215 is connected to the single transverse passage 217 in the upper surface 219 in the second leg. The pipe 221 connects to the longitudinal passage 215 and runs up the outside of the first leg 201, and is retained by the clamp 213.

The internal passage arrangement can be connected to a vacuum line, which enables blood and other fluids to be aspirated from the vicinity of the fan retractor. Such an arrangement can also be used to aspirate the smoke generated by electrocautery, a process commonly used in laparoscopic procedures.

The internal passage arrangement can be connected to a suitable syringe, pump, or water line, so that fluids can be infused into the vicinity of all or parts of the second legs. The fluids can be infused into the abdomen if the fan retractor is used conventionally, or into the space between the peritoneum and the properitoneal fat layer, if the fan retractor is used properitoneally. For example, saline can be infused for irrigation. In another example, a suitable insufflation gas can be infused for pneumoperitoneum. In procedures using local anaesthesia, a spray of anaesthetic can be sprayed into the abdomen from the fan retractor.

In the arrangement with two longitudinal passages and connecting transverse passages shown in FIG. 7A, the longitudinal passage 215 and transverse passage 217 can be used for infusion, and the longitudinal passage 205 and plurality of transverse passages, such as the transverse passage 207, can be used for aspiration.

In the embodiment of a fan retractor having second legs with an internal passage arrangement shown in FIG. 7B, the second leg 302 is attached to the first leg 301. The second leg has a longitudinal passage 305, connected to a plurality of transverse passages, including the transverse passage 307, that connect to the lower surface 309 of the second leg. A plurality of optical fibres 331 is inserted into the longitudinal passage 305 through the proximal end 211 of the second leg. Individual fibres, such as the fibre 333, or groups of fibres, are brought to the lower surface 309 through the transverse passages, such as the transverse passage 307.

The proximal end 335 of the plurality of optical fibres is connected to a suitable light source 337. Light from the light source is emitted from the ends of the fibres, such as the end of the fibre 333, in the lower surface 309 of the second legs and provides working light for the surgeon to treat the tissue being treated. The peritoneum is sufficiently translucent that light emitted from optical fibres in the second legs of the fan retractor will provide adequate working light even when the retractor is inserted properitoneally.

Instead of inserting a plurality of optical fibres into passages in the second leg, the optical fibres can be molded integrally with the second leg as part of the process of molding the second leg blanks.

FIG. 7C shows an alternative arrangement in which the first leg 401 is formed using a hollow tube, the bore of which connects to the internal passage arrangement of the second leg. In the example shown, the plurality of optical fibres 431 passes through the bore of the first leg into the longitudinal passage 405, and individual fibres, such as the fibre 433, are brought out to the lower surface 409 of the second legs through a plurality of transverse passages, such as the passage 407. Otherwise, the construction of the second leg 402 is similar to the second leg 302 in FIG. 7B, and will not be described further.

The first leg 401 is extended through the leg actuator 404 to allow the plurality of optical fibres 431 to emerge from the bore of the first leg thus exposed. FIG. 7C shows a simple form of the fan retractor that lacks a lifting force indicator (FIGS. 5A through 5C, and 6A). In fan retractors equipped with additional lifting force indicators (FIG. 6A), the additional lifting force indicator has to be relocated to provide room for the plurality of optical fibres.

FIG. 7C shows an embodiment of the fan retractor having a plurality of optical fibres inserted in the internal passages of the second leg 402. Alternative versions of the embodiment of FIG. 7C can be made in which the internal passages are used for infusion or aspiration. In these, the infusion or aspiration pipe (similar to the pipes 211 and 221 in FIG. 7A) can be run inside the bore of the first leg 410. If the second leg has multiple internal passages, multiple pipes and optical fibres can be run through the bore of the first leg.

A method of using a single fan properitoneal retractor to lift the abdominal will next be described.

An incision, 0.4"–0.8" (10–20 mm) long is made in a suitable location in the abdominal wall. The incision is made through the skin, the subcutaneous fat, muscle and fascia, until the properitoneal fat layer is reached, just short of the peritoneum.

The operating levers 114 (FIG. 8D) of the fan retractor 103 are manipulated to bring the second legs 102 fan retractor to their closed state if they are not in this state already. The distal ends 149 of the second legs are then inserted into the incision and pushed through the incision until they abut against the peritoneum. The pressure of the wide, gently curved distal ends of the second legs against the peritoneum detaches the peritoneum from the properitoneal fat layer without piercing the peritoneum. The distal ends of the second legs are worked into the space between the peritoneum and the properitoneal fat layer. The retractor is then advanced along the center line CL of the abdomen (FIG. 8B), keeping the angle between the second legs and the abdominal wall as small as possible to minimize detachment of the peritoneum. Advancing the second legs progressively detaches the peritoneum from the properitoneal fat layer.

Figure 8A:
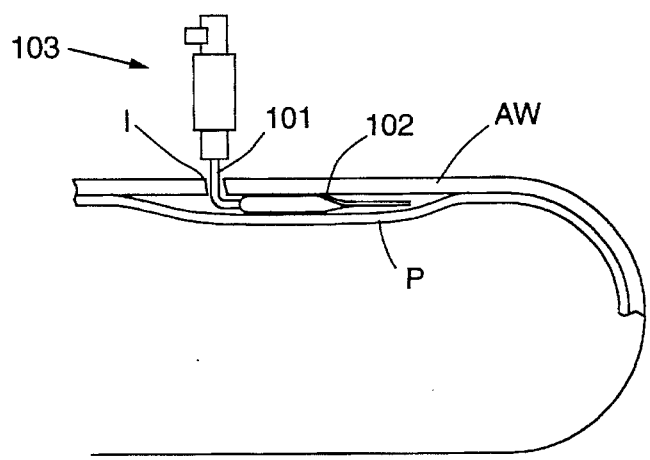
FIGS. 8A through 8D illustrate the method of using a properitoneal fan retractor properitoneally to lift the abdominal wall.
Figure 8B:
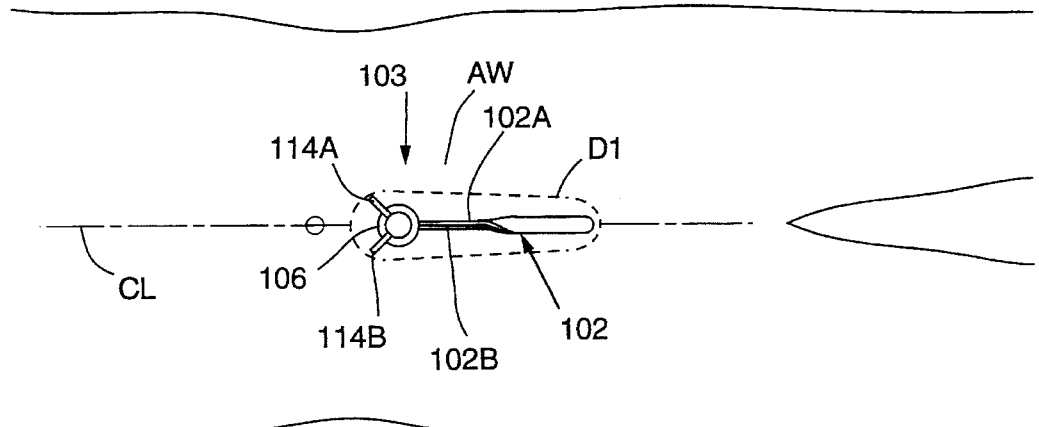

The first legs 101 abutting against the incision I limits the advancing of the second legs 102, as shown in FIG. 8A. The orientation of the second legs relative to the center line CL of the abdomen is checked, and the second legs are reoriented if necessary to align them along the center line (FIG. 8B). Since the second legs 102 have a fixed orientation relative to the main mounting block 106, orientation marks on the main mounting block can be used to indicate the direction of the second legs. The outline of the part of the peritoneum detached from the properitoneal fat layer is shown by the broken line $D_1$ in FIG. 8B.

Figure 8C:
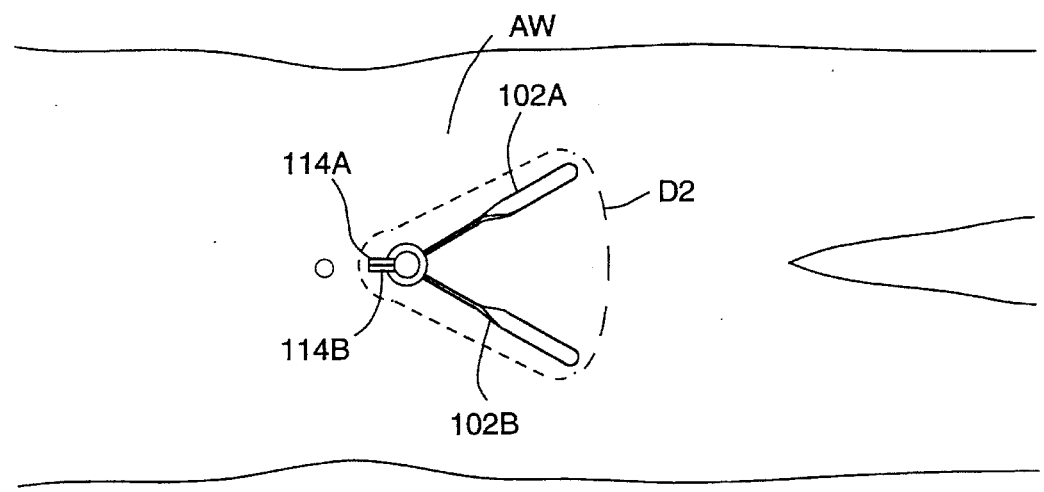

The operating levers 114A and 114B are then squeezed together to force the second legs 102A and 102B apart, as shown in FIG. 8C. In moving apart, the second legs detach more of the peritoneum from the properitoneal fat layer, as shown by the dotted line $D_2$. While squeezing the operating levers, the orientation of the main mounting block 106 is observed to ensure that any asymmetrical resistance to the opening of the second legs does not skew the symmetrical placement of the second legs relative to the center line CL. Since the second legs open symmetrically with respect to the main mounting block, any skewing of the second legs can be observed as rotation of the main mounting block. An appropriate torque applied to the main mounting block can be used to correct any skewing that occurs, and ensure that the second legs are symmetrically placed.

Figure 8D:
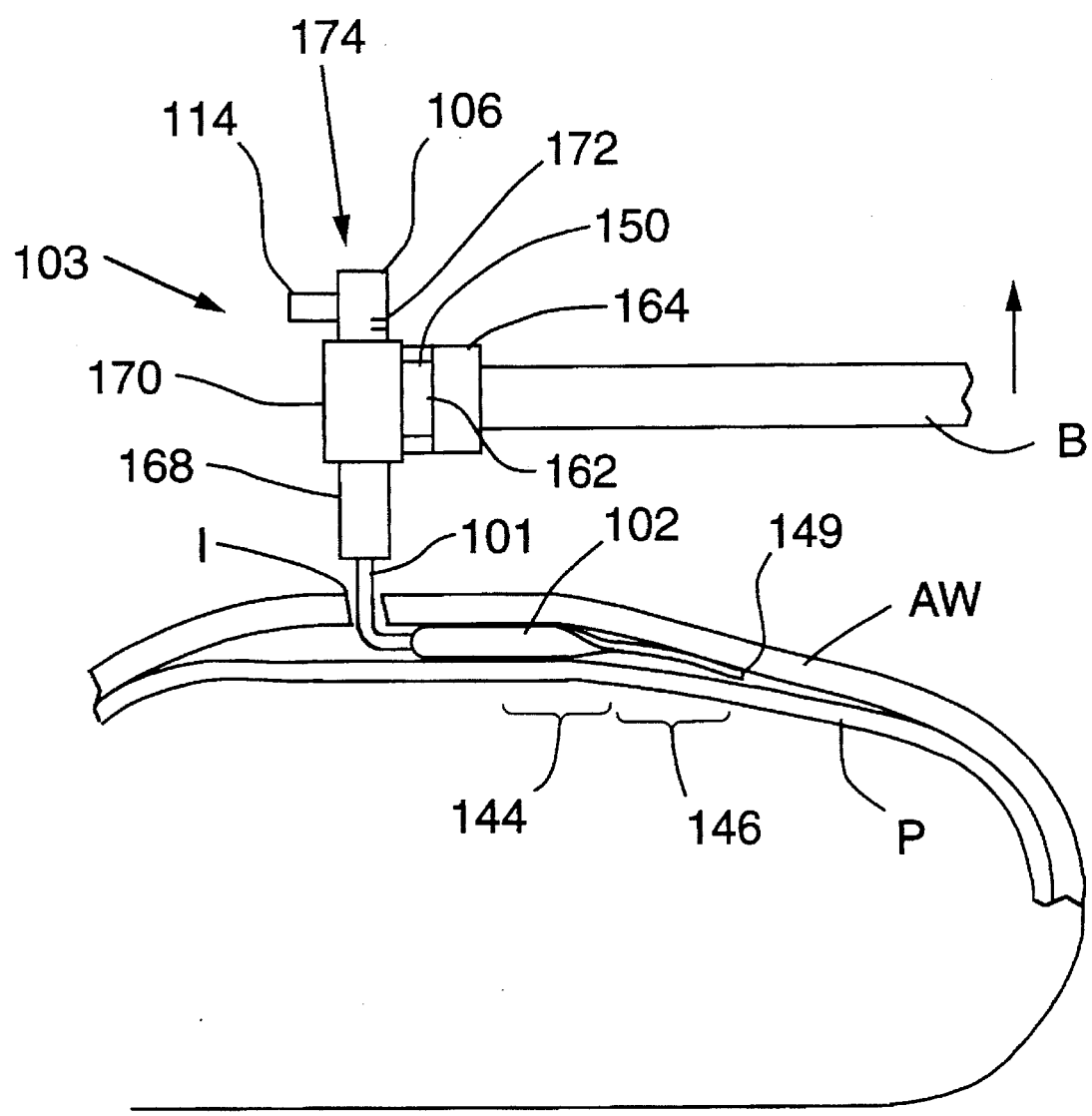

The male dovetail connector 150 is coupled to the female dovetail connector 162 on the lifting arm adaptor 164, as shown in FIG. 8D. The lifting arm adaptor is attached to the lifting arm B by conventional means (not shown). The main mounting block can rotate relative to the mounting sleeve, so the orientation of the lifting arm relative to the second legs may be changed from that shown, if desired. The lifting arm B is then raised progressively while watching one of the lifting force indicators, the scale 172 on the cylindrical wall of the main mounting block 106, or the additional lifting force indicator 174 in the end face of the main mounting block. If the lifting force comes close to the allowable limit for the procedure, the lifting force can be reduced by reducing the rate of lifting, or stopping the lifting altogether.

As the lifting force applied to the retractor increases, and the abdomen becomes more curved as a result of being lifted, the third and fourth parts 144 and 146 of the second legs bend to conform with the shape of the inside of the abdominal wall, as shown in FIG. 8D. The bending and the relatively large width of the distal parts of the second legs, and the symmetrical placing of the second legs within the abdomen, substantially reduce the risk of the ends 149 of the second legs traumatizing or penetrating the abdominal wall AW.

Once the required amount of lifting has been obtained, the lifting arm B is locked in position, and the treatment procedure is carried out. The incision I may be carried through the peritoneum, and used to insert endoscopes or other instruments into the abdomen. The incision I can be put to further use because the first legs 101 of the retractor occupy only a relatively small part of the incision.

If the second legs of the retractor have longitudinal passages, these may be used during the treatment procedure to provide illumination of the treatment area, and infusion and aspiration of the properitoneal area.

After treatment has been completed, the lifting arm B is progressively lowered to return the abdomen to its normal state. When the direction of the lifting force applied to the dovetail connector reverses, the dovetail connector automatically disconnects. This informs the operator that the lifting arm has been lowered far enough, and also prevents the lifting arm from driving the retractor into the abdomen and causing compression injury to the underlying bowel.

The operating levers 114 are moved apart to bring the second legs 102 together once more. The fan retractor 103 is then manipulated to withdraw the second legs from under the peritoneum through the incision I.

The properitoneal retraction method just described is preferably practiced using a properitoneal fan retractor of the type described above, which is specially designed for this purpose. However, this is not a requirement for practicing the above properitoneal retraction method. The method can be practiced using other suitable retractors.

Properitoneal retraction is preferred because interposing the peritoneum between the retractor and the underlying bowel and omentum prevents the retractor from snagging the bowel or omentum. This makes the process of inserting the retractor easier, and less risky.

The fan retractor described above is not limited to properitoneal use. Most of the advantages conferred by the fan retractor described above can also be obtained when the fan retractor is used in the abdomen to exert its lifting force against the posterior face of the peritoneum.

The method set forth above can easily be adapted for use in the abdomen. The incision I is carried through the peritoneum. The abdomen is preferably insufflated before the second legs of the retractor are inserted through the incision. Insufflation provides a clearance between the second legs of the retractor and the underlying bowel and omentum. A third incision is required for an endoscope to observe placement of the second legs.

When the second legs are inserted into the abdomen, care must be taken to ensure that they are kept as close to the abdominal wall as possible to reduce the chance of snagging bowel or omentum. The insertion process and the leg spreading process must be carried out under continuous observation to check for snagging. If snagging occurs, the second legs must be withdrawn, at least partially, to release the snag, and the insertion process recommenced.

Providing illumination in the vicinity of the second legs using a plurality of optical fibres inserted into internal passages in the second legs makes it easier to see snags than conventional illumination methods.

Once the second legs have been fully inserted and it is confirmed that they do not snag anything, the fan retractor is used to lift the abdominal wall, as described above.

The single fan retractor raised by a lifting arm as described above functions well in patients of normal body habitus and in mildly obese patients. It also functions well in procedures that involve manipulations and dissection of tissue and organs situated in the center of the abdomen. Inadequate visualization and working space occurs when a single fan retractor is used in obese and morbidly obese patients, and in procedures in normal patients where access to lateral regions of the abdominal cavity, such as the paracolic gutters, is required.

The method according to the invention of raising the abdominal wall to provide adequate working space and visualization in obese and morbidly obese patients, and to provide improved working space and visualization in the lateral regions in normal patients uses two fan retractors inserted properitoneally at right angles relative to the placement of the fan retractors in the one-retractor method described above. The two fan retractors are inserted laterally, substantially along the center line of the abdomen, and are separated from one another by a few inches. To enable two spatially-separated fan retractors to lift the abdominal wall uniformly, the fan retractors are connected to a crossbar according to the invention. The crossbar is connected to the lifting arm.

The crossbar according to the invention will first be described with reference to FIGS. 9A through 9E. FIG. 9A shows a plan view of the crossbar 500 in which all the major components are shown. Attached to the bar 502 is the lifting arm connector 504, which preferably is a male dovetail connector. The first and second retractor mounts 506 and 508, respectively, are mounted on the bar 502 and are free to slide along the length of the bar. Each of the retractor mounts 506 and 508 includes a retractor connector 510 and 512, respectively. Each of the retractor mounts 506 and 508 can be locked in place on the bar 502 with a locking device 514 and 516, respectively.

Figure 10A:
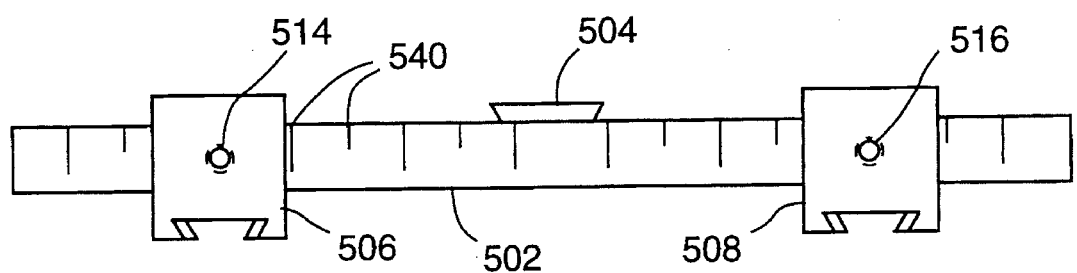
Figure 10B:
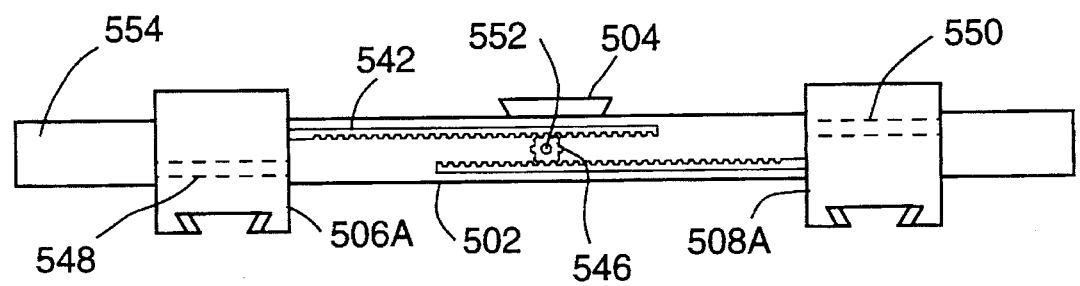
Figure 10C:
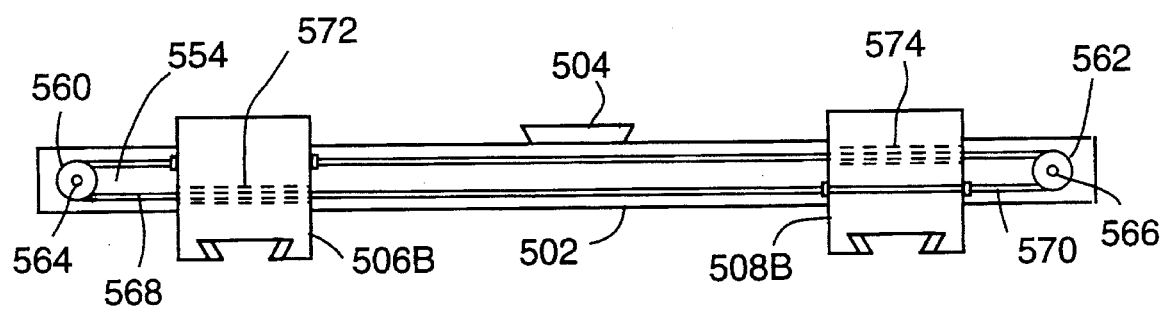

The bar 502 is preferably a piece of stainless steel about 12" (300 mm) long, with a square cross section about 0.5" (12 mm) on a side, as shown in FIGS. 10B and 10C. Metals other than stainless steel could be used; alternatively, the bar could be made from a fibre-reinforced plastic. Although the preferred cross section of the bar 502 is square, it could be rectangular, triangular, or any other cross section that would prevent the retractor mounts 506 and 508 from turning about the longitudinal axis of the bar. A bar having a circular cross section with a keyway can also be used.

The lifting arm connector 504 is attached to the bar 502 halfway along the length of the bar. The preferred method of attaching the lifting arm connector to the bar is by welding, although the lifting arm connector could be attached by a suitable adhesive, or by screws, by nuts and bolts, or by some other suitable method. When a male dovetail connector is used for the lifting arm connector, a male dovetail connector having the same dimensions as the male dovetail connector used on the preferred fan retractor is preferred. This enables the crossbar 500 to be connected to the end of a lifting arm having a female dovetail connector adapted for connecting to a single fan retractor by mating the male dovetail connector on the crossbar with the female dovetail connector on the lifting arm.

Connectors other than a male dovetail connector may be used for the lifting arm connector 504, if desired. The genders of the dovetail connectors may be reversed, if desired. The crossbar may alternatively be permanently attached to the lifting arm.

The crossbar may be made more versatile by affixing a different connector to opposite faces of the bar 502. For example, different sizes of male dovetail connector can be provided.

The retractor mounts 506 and 508 each have a body 507 and 508, respectively. Each body is preferably substantially a cube with each side about 1.1" (28 mm) long. An end elevation and a cross section of the retractor mount 506 is shown in FIGS. 9D and 9E, respectively. The retractor mounts are preferably made of stainless steel, although other suitable metals or plastics could be used. The retractor mounts can be cast or molded, milled from a single piece of metal, or fabricated.

A retractor connector 510 is formed in the front face 522 of the retractor mount 506, preferably by milling. The retractor connector can alternatively be attached to the front face 522. The retractor connector is preferably a female dovetail connector dimensioned to accept the male dovetail connector on the preferred fan retractor to enable a preferred fan retractor to be connected to the retractor mount.

It is highly desirable that at least one of the lifting arm connector and the retractor connectors be unidirectional such that when the direction of the lifting force is reversed, the connector disconnects. This is to prevent a downward force from being applied to the fan retractors, which could cause the fan retractors to damage the underlying bowel or omentum. A dovetail connector is one example of a unidirectional connector.

The bar hole 526 is formed in the retractor mount 506. The bar hole is dimensioned so that the retractor mount is a slip fit on the bar 502. The bar hole 526 is located so that it is vertically centered in the retractor mount and is horizontally offset so that it is symmetrically placed between the back 518 of the retractor connector 510 and the back face 520 of the retractor mount 506.

A threaded hole 524 is formed in the retractor mount 506 from the top face 528 to the central hole 526. A suitable screw is inserted into the threaded hole to provide the locking device 514 which locks the retractor mount 506 in position along the length of the bar 502 after the position of the retractor mount has been adjusted. A grub screw operated by an Allen wrench can be used; preferably, a knurled thumbscrew is used. Other types of devices, such as an over-center clamp, can be used to provide the locking device 514.

The retractor mount 508 is identical to the retractor mount 506, and will not be separately described. The retractor mount 508 is mounted on the bar 502 on the opposite side of the lifting arm connector 504 from the retractor mount 506.

The retractor mounts 506 and 508 need to be disposed along the length of the bar 502 symmetrically about the lifting arm connector 504 to distribute the lifting force applied to the crossbar 500 equally between the fan retractors. A number of alternative arrangements for ensuring that the retractor mounts are symmetrically disposed are shown in FIGS. 10A through 10D.

In FIG. 10A, the positions of the retractor mounts 506 and 508 along the length of the bar 502 can be independently adjusted. The bar is marked along its length with markings 540, which are disposed symmetrically about the lifting arm connector 504. The symmetrically-placed markings 540 assist the surgeon to position the retractor mounts symmetrically relative to the mail dovetail connector.

Preferably, after the fan retractors have been inserted, the locking devices 514 and 516 are released, the fan retractors are attached to their respective retractor mounts 506 and 508, a gentle lifting force is applied, preferably by hand, and the bar is slid through the retractor mounts until the markings 540 indicate that the retractor mounts are symmetrically placed. The locking devices are then locked, and the crossbar is attached to the lifting arm.

Figure 10D:
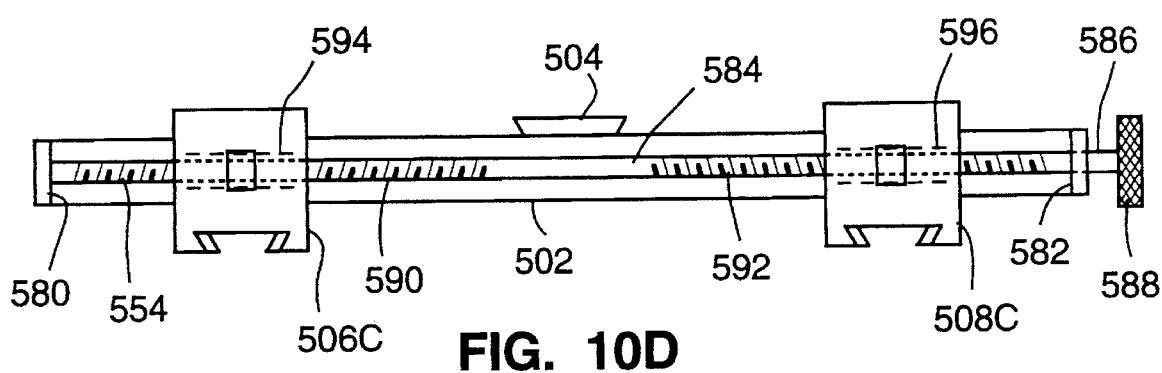

FIGS. 10B through 10D show three arrangements in which the retractor mounts are incapable of independent movement, and, instead, are constrained to move symmetrically about the lifting arm connector 504.

In FIG. 10B, a toothed rack 542 and 544 is attached to each of the retractor mounts 506A and 508A, respectively. The retractor mounts 506A and 508A are similar to the retractor mounts 506 and 508, respectively, described above. Differences are the toothed racks, and a rack channel 548 and 550 formed in each retractor mount 506A and 508A, respectively, to accommodate the rack 544 and 542, respectively, of the other retractor mount when the retractor mounts are closely spaced.

The toothed racks 542 and 544 engage with opposite sides of the pinion 546, which rotates freely on an axle attached to the center of the bar 502. The racks and pinion are assembled so that the retractor mounts 506A and 508A are symmetrically disposed about the lifting arm connector 504. Movement of one of the retractor mounts along the length of the bar imparts through the rack and pinion arrangement an equal and opposite motion of the other retractor mount, which keeps the retractor mounts symmetrically disposed at all times. With this arrangement, one of the locking devices (not shown) may be dispensed with because locking one of the retractor mounts locks the other retractor mounts.

In FIG. 10B, the rack and pinion mechanism is shown mounted on the upper face 554 of the bar 502. The mechanism may be mounted on other faces of the bar, or may be built into the bar.

In FIG. 10C, pulleys 560 and 562 are mounted on axles 564 and 566, respectively, at opposite ends of the bar 502. A first cord 568 has one end attached to the retractor mount 506B. The first cord passes around the pulley 560 and through a bore 572 in the retractor mount 506B. The other end of the first cord is attached to the retractor mount 508B. A second cord 570 has one end attached to the retractor mount 508B. The second cord passes around the pulley 562 and through a bore 574 in the retractor mount 508B. The other end of the first cord is attached to the retractor mount 506B. The retractor mounts 506B and 508B are otherwise the same as the retractor mounts 506 and 508, respectively, described above.

The cords, pulleys and retractor mounts are assembled so that the retractor mounts 506B and 508B are symmetrically disposed about the lifting arm connector 504. Movement of one of the retractor mounts along the length of the bar imparts through the cord and pulley arrangement an equal and opposite motion of the other retractor mount, which keeps the retractor mounts symmetrically disposed at all times. With this arrangement, one of the locking devices (not shown) may be dispensed with because locking one of the retractor mounts locks the other retractor mounts.

In FIG. 10C, the cord and pulley mechanism is shown mounted on the upper face 554 of the bar 502. The mechanism may alternatively be mounted on other faces of the bar, or may be built into the bar.

In FIG. 10D, brackets 580 and 582 attach the lead screw 584 to the bar 502. The brackets 580 and 584 also locate the lead screw longitudinally relative to the bar. An extension 586 of the lead screw projects beyond the bar and has the knurled knob 588 attached to it. The lead screw has two threaded portions 590 and 592 substantially symmetrically disposed about the lifting arm connector 504. The threaded portion 590, distal from the knob 588 is, for example, right-hand threaded; the threaded portion 592, proximal to the knob 588, is opposite threaded with the same thread pitch. For example, the threaded portion 592 is left-hand threaded.

The lead screw passes through bores 594 and 596 in the retractor mounts 506C and 508C. The lead screw followers 596 and 598 engage with the threaded portions 590 and 592, respectively, and are attached to the retractor mounts 506C and 508C. The retractor mounts 506C and 508C are otherwise the same as the retractor mounts 506 and 508, respectively, described above.

The retractor mounts 506C and 508C are assembled on the lead screw 585, and the lead screw is assembled in the bar 502 so that the retractor mounts 506C and 508C are symmetrically disposed about the lifting arm connector 504. Rotating the knurled knob 588 in one direction moves the retractor mounts along the length of the bar symmetrically towards one another. Rotating the knurled knob in the opposite direction moves the retractor mounts symmetrically away from one another. With this arrangement, both the locking devices (not shown) may be dispensed with because the lead screw holds the retractor mounts in position along the length of the bar.

In FIG. 10D, the lead screw mechanism is shown mounted on the upper face 554 of the bar 502. The mechanism may alternatively be mounted on other faces of the bar, or may be built into the bar.

The method according to the invention will now be described with reference to FIGS. 11A through 11F. As an example, use of the method according to the invention in the course of performing a laparoscopic cholecystectomy will be described.

Figure 11A:
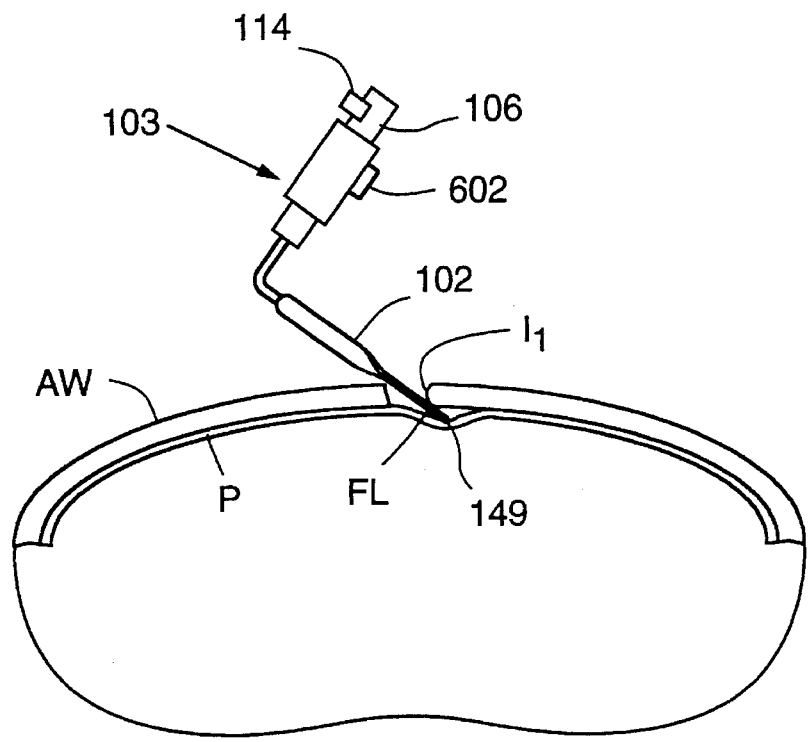

A first incision $I_1$, 0.4"–0.8" (10–20 mm) long is made in a suitable location in the abdominal wall AW, as shown in FIG. 11A. The incision is made through the skin, the subcutaneous fat, muscle and fascia, until the properitoneal fat layer is reached, just short of the peritoneum P. The preferred location of the incision $I_1$ is in the umbilicus.

The operating levers 114 of the fan retractor 103 are manipulated to bring the second legs 102 fan retractor to their closed state if they are not in this state already.

The fan retractor is placed with the distal ends 149 of its second legs inserted into the incision $I_1$. The second legs 102 of the fan retractor are directed laterally towards the right paracolic gutter, instead of being directed towards the right upper quadrant as when a single fan retractor is used. The distal ends of the second legs are pushed through the incision until they abut against the peritoneum P. The pressure of the wide, gently curved distal ends of the second legs against the peritoneum detaches the peritoneum from the properitoneal fat layer FL without piercing the peritoneum. The distal ends 149 of the second legs are worked into the space between the peritoneum and the properitoneal fat layer. The retractor is then advanced laterally towards the right paracolic gutter. The angle between the second legs and the abdominal wall is kept as small as possible to minimize detachment of the peritoneum. Advancing the second legs progressively detaches the peritoneum from the properitoneal fat layer.

Figure 11B:
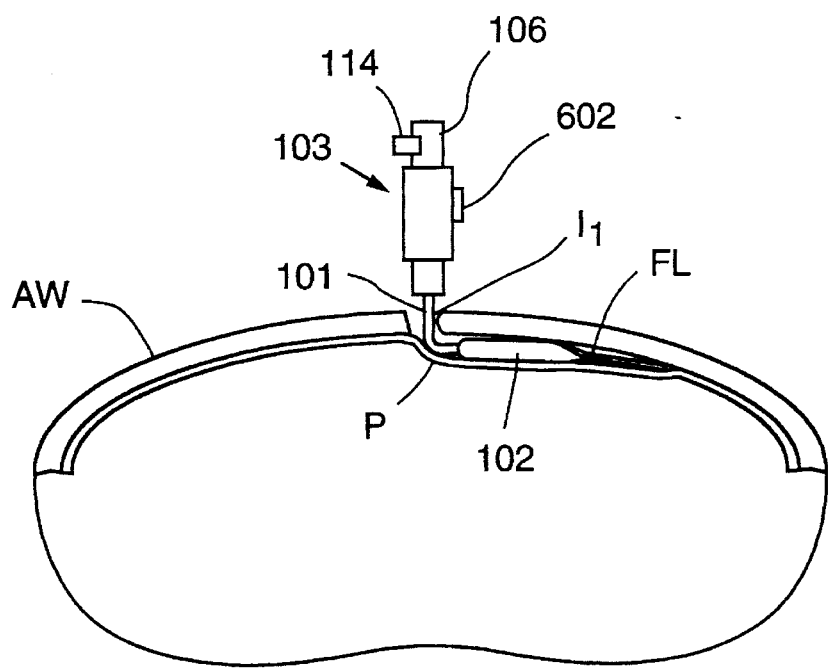

The first legs 101 abutting against the incision $I_1$ limits the advancing of the second legs 102, as shown in FIG. 11B. The orientation of the second legs to the desired insertion direction is checked, and the second legs are reoriented if necessary. Since the second legs 102 have a fixed orientation relative to the main mounting block 106, orientation marks on the main mounting block can be observed to determine the direction of the second legs.

Figure 11C:
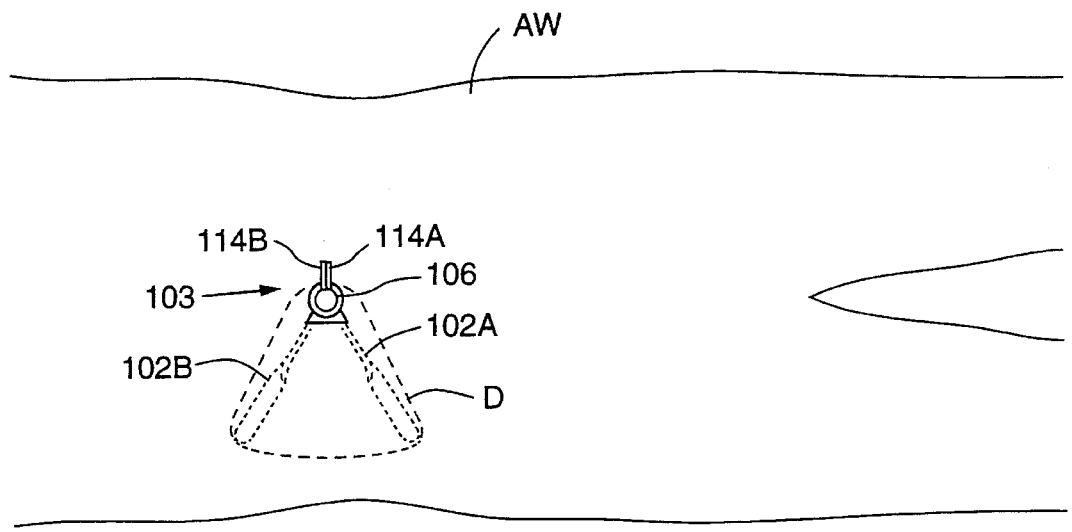

The operating levers 114A and 114B are then squeezed together to force the second legs 102A and 102B apart, as shown in FIG. 11C. In moving apart, the second legs detach more of the peritoneum from the properitoneal fat layer, as shown by the dotted line D. While squeezing the operating levers, the orientation of the main mounting block 106 is observed to ensure that any asymmetrical resistance to opening the second legs does not skew the symmetrical placement of the second legs relative to the desired insertion direction. Since the second legs open symmetrically with respect to the main mounting block, any skewing of the second legs can be observed as rotation of the main mounting block. An appropriate torque applied to the main mounting block can be used to correct any skewing that occurs, and ensure that the second legs are symmetrically placed.

Figure 11D:
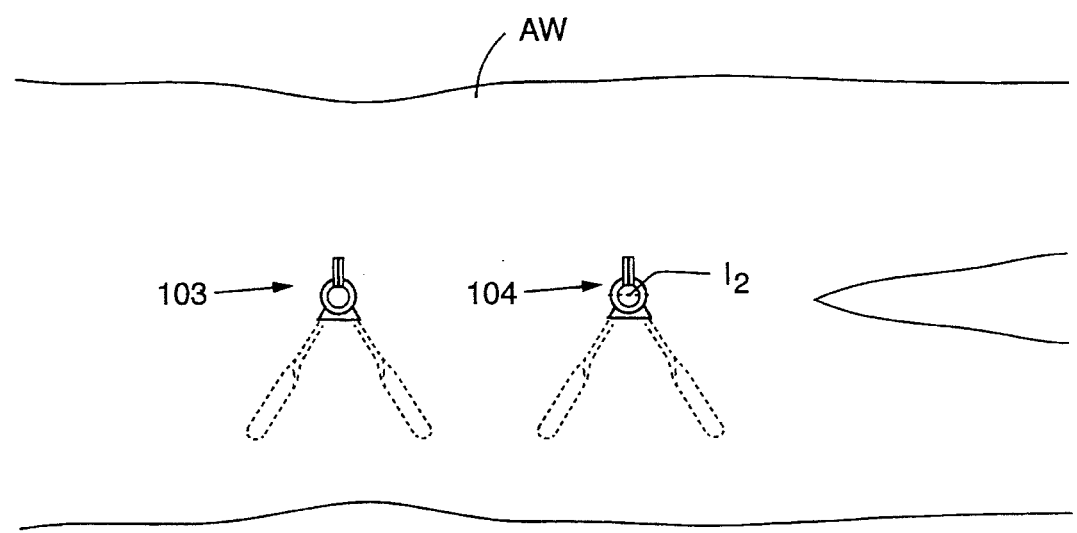

A second incision $I_2$ is made in the abdominal wall substantially on the abdominal center line, as shown in FIG. 11D. The second incision is made through the abdominal wall as far as the properitoneal fat layer. The second legs of a second fan retractor 104 are inserted into the second incision as far as the peritoneum and are advanced laterally between the peritoneum and the properitoneal fat layer towards the right paracolic gutter. Once the second legs of the second fan retractor are fully inserted, they are spread apart, as shown in FIG. 11D. The method of inserting the second fan retractor is substantially the same as the method of inserting the first fan retractor, and so will not be described in detail. More details of the process for inserting a fan retractor both properitoneally and abdominally can be found in the description of the method for inserting a single fan retractor set forth above.

The second incision is preferably located at the epigastric point where the incision for inserting the gallbladder dissector and clip applier is normally located. Once the second legs of the second fan retractor have been fully inserted, the second incision can be continued through the peritoneum so that, after the abdominal wall has been raised, the second incision can also be used to insert the gallbladder dissector and the clip applier.

Although the preferred method of lifting the abdominal wall includes placing the second legs of the fan retractors properitoneally, the method may also be practiced with the fan retractors placed abdominally. In addition, although the flexible second legs of the fan retractors described above make such fan retractors especially suitable for lateral placement in the abdomen, the method according to the invention may be practiced using other types of fan retractors. Furthermore, although the method is preferably practiced using fan retractors, the method may also be practiced using angle-shaped hook retractors with second legs about 4" to 6" (100 to 150 mm) long. The hook retractors preferably would have flexible second legs like the fan retractors described above, but rigid-legged hook retractors can also be used.

Figure 11E:
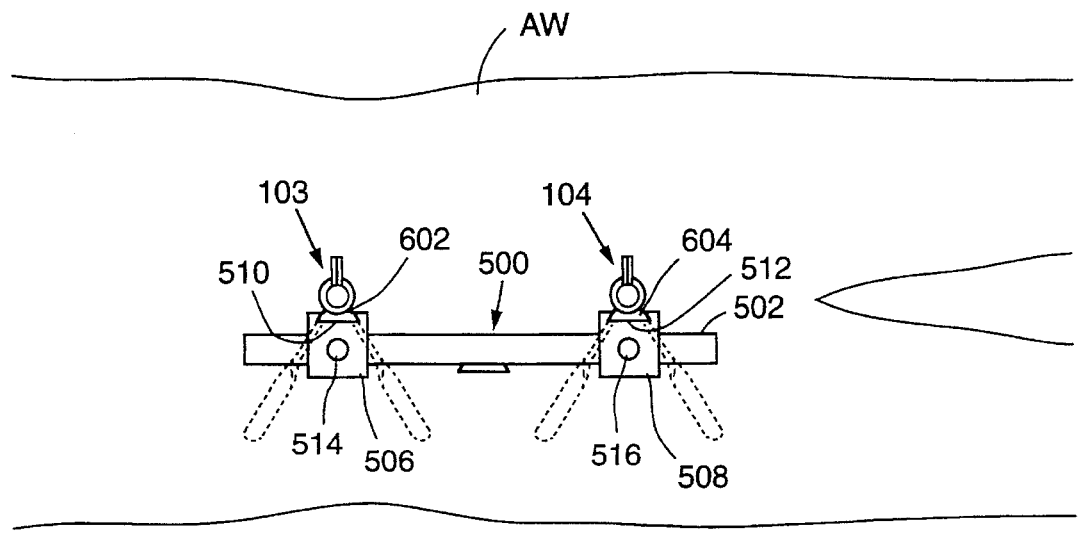

Once both fan retractors have been inserted, they are connected to the crossbar 500 according to the invention, as shown in FIG. 11E. The locking devices 514 and 516 on the crossbar are released to allow the retractor mounts 506 and 508, respectively, to slide freely along the bar 502. The fan retractor 103 is connected to the retractor mount 506 by mating the lifting arm connector 602 on the fan retractor 103 with the retractor connector 510 on the retractor mount 506. The fan retractor 104 is connected to the retractor mount 508 by mating the lifting arm connector 604 on the fan retractor 104 with the retractor connector 512 on the retractor mount 508.

The longitudinal position of the bar 502 is then adjusted so that the retractor mounts 506 and 508 are positioned symmetrically with respect to the lifting arm connector 504. The locking devices 514 and 516 are then activated to lock the first and second retractor mounts in position on the bar. Centering the retractor mounts with respect to the lifting arm connector ensures that the lifting force is balanced between the two fan retractors 103 and 104, and prevents excessive pressure being applied to one lifting site relative to the other.

Figure 11F:
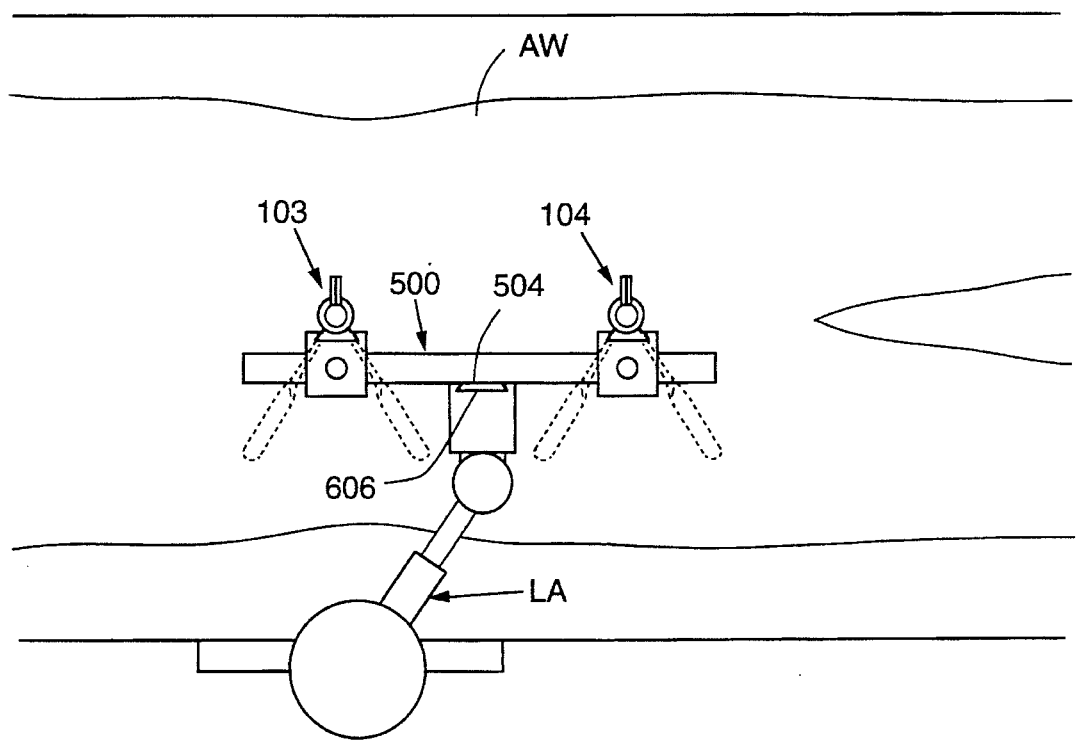

The crossbar is then connected to the lifting arm by mating the lifting arm connector 504 with the female dovetail connector 606 on the lifting arm LA, as shown in FIG. 11F. The lifting arm is then operated to raise the lifting arm connector, which, via the bar, the retractor mounts, and the two fan retractors, raises a greater area of the abdomen compared with using a single fan retractor, and provides a generous amount of visualization and working space in obese and morbidly obese patients, and in the lateral regions of the abdomen in normal patients.

In procedures requiring access to the left side of the abdomen, the same procedure is used with the fan retractors inserted laterally towards the left paracolic gutter.

We claim:

1. An apparatus for use in a surgical procedure to connect a first retractor and a second retractor each including a connector half of a first type to a mechanical lifting arm including a connector half of a second type to raise a tissue plane of the body, the retractors requiring application of a lifting force and a lifting torque to lift the tissue plane, the lifting torque being applied about an axis generally perpendicular to the lifting force, part of the retractors being inserted into the body, internal of the epidermis, to transmit the lifting force, the apparatus comprising:

a bar, having a center, the bar being elongate and defining a longitudinal axis;

a first connecting means including a connector half of the second type capable of mating with the connector half of the first type of the first retractor, slidably mounted on the bar and lockable to the bar, for detachably and rigidly connecting the first retractor to the bar, the first connecting means transmitting the lifting force and the lifting torque from the bar to the first retractor and generally preventing the first retractor from moving relative to the bar;

a second connecting means including a connector half of the second type capable of mating with the connector half of the first type of the second retractor, slidably mounted on the bar and lockable to the bar, for detachably and rigidly connecting the second retractor to the bar, the second connecting means transmitting the lifting force and the lifting torque from the bar to the second retractor and generally preventing the second retractor from moving relative to the bar;

a third connecting means, attached to the center of the bar including a connector half of the first type capable of mating with the connector half of the second type of the mechanical lifting arm, for detachably and rigidly connecting the bar to the mechanical lifting arm, the third connecting means transmitting the lifting force and the lifting torque from the mechanical lifting arm to the bar, and generally preventing the bar from moving relative to the mechanical lifting arm; and wherein the lifting force has a direction to lift the tissue plane and each connector half of the first type automatically disconnects from the respective connector half of the second type in response to a force in a direction opposite to the direction of lifting force.

2. The apparatus of claim 1, wherein the first connecting means and the second connecting means each comprise:

a connector body having a hole therethrough adapted for receiving the bar; and, locking means for locking the body to the bar.

3. The apparatus of claim 2, wherein the locking means comprises:

a threaded hole in the body, substantially perpendicular to the longitudinal axis, and a screw engaging with the threaded hole.

4. The apparatus of claim 2, wherein the locking means comprises a means for clamping the bar.

5. The apparatus of claim 1, additionally comprising symmetry means for disposing the first connecting means and the second connecting means symmetrically about the third connecting means.

6. The apparatus of claim 5, wherein the symmetry means comprises marks on the bar symmetrically disposed about the third connecting means.

7. The apparatus of claim 5, wherein the symmetry means comprises:

a pinion rotatably attached to the bar, a first rack attached to the first connecting means, and engaging with the pinion, a second rack attached to the second connecting means, and engaging with the pinion, the first rack and the second rack engaging with opposite sides of the pinion.

8. The apparatus of claim 5, wherein the symmetry means comprises:

a first pulley and a second pulley disposed at opposite ends of the bar, a first thread having a first end attached to the first connecting means, the thread passing through the second connecting means and around the second pulley, and having a second end attached to the second connecting means, and a second thread having a first end attached to the second connecting means, the thread passing through the first connecting means and around the first pulley, and having a second end attached to the first connecting means.

9. The apparatus of claim 1, wherein:

the third connecting means is offset horizontally and laterally relative to the longitudinal axis, and the first connecting means and the second connecting means are each offset horizontally and laterally relative to the longitudinal axis.

10. The apparatus of claim 9, wherein the connector half of the first type is attached to the bar on an opposite side of the longitudinal axis from the connector half of the second type.

11. An apparatus for use in a surgical procedure to connect a first retractor, including a male half of a dovetail connector, and a second retractor, also including a male half of a dovetail connector, to a mechanical lifting arm including a female half of a dovetail connector to raise a tissue plane of the body, the retractors requiring application of a lifting force and a lifting torque to lift the tissue plane, the lifting torque being applied about an axis generally perpendicular to the lifting force, part of the retractors being inserted into the body, internal of the epidermis, to transmit the lifting force, the apparatus comprising:

a bar, having a center, the bar being elongate and defining a longitudinal axis;

first and second retractor connectors slidably mounted on the bar, each retractor connector including:

a connector body having a hole therethrough adapted for receiving the bar, a female half of a dovetail connector coupled to the connector body and capable of mating with the male half of a dovetail connector of one of the first retractor and the second retractor, the male half of a dovetail connector of the one of the first retractor and the second retractor and the female half of a dovetail connector coupled to the connector body, when mated, transmitting the lifting force and the lifting torque from the connector body to the one of the first retractor and the second retractor while preventing the one of the first retractor and the second retractor from moving relative to the bar, and locking means for locking the connector body to the bar; and a male half of a dovetail connector, attached to the center of the bar, and capable of mating with the female half of a dovetail connector of the lifting arm, the male half of a dovetail connector attached to the bar and the female half of a dovetail connector of the lifting arm, when mated, transmitting the lifting force and the lifting torque from the mechanical lifting arm to the bar while preventing the bar from moving relative to the mechanical lifting arm.

12. The apparatus of claim 11, wherein the locking means comprises:

a threaded hole in the body, substantially perpendicular to the longitudinal axis, and a screw engaging with the threaded hole.

13. The apparatus of claim 11, wherein the locking means comprises means for clamping the bar.

14. In combination with a mechanical lifting arm and a pair of mechanical retractors insertable through small laparoscopic openings in the body to lift a tissue plane of the body, an improved apparatus for connecting the retractors to the mechanical lifting arm for select movement towards and away from one another so that the relative positions of the retractors can be adjusted and lifting force and torque can be transmitted to the retractors from the lifting arm, said apparatus comprising:

an elongated rigid bar;

first connecting means secured in load and torque transmitting relationship with one of said retractors, said first connecting means being slidably mounted on the bar and lockable to the bar to selectively secure said one retractor in torque and load transmitting relationship to the bar at different positions along the length of the bar;

second connecting means secured in load and torque transmitting relationship with the other of said retractors, said second connecting means being slidably mounted on the bar and lockable to the bar to selectively secure said other retractor in torque and load transmitting relationship to the bar at different positions along the length of the bar and to, together with the first connecting means, adjust the distance between the retractors; and third connecting means attached to the bar between the first and second connecting means to selectively secure the bar to the lifting arm and transmit lifting force and torque from the arm to the bar.

15. In a combination according to claim 14, the improved apparatus wherein the first and second connecting means are releasably secured in load and torque transmitting relationship with the retractors by tongue and groove connectors.

16. In a combination according to claim 15, the improved apparatus wherein the tongue and groove connectors are arranged to slidably disengage in response to force in a direction opposite to the direction of the lifting force.

17. In a combination according to claim 14, the improved apparatus wherein: the bar is of a rectangulinear configuration having a longitudinal axis; and the first and second connecting means are slidably mounted on the bar and keyed thereto against movement about said longitudinal axis.

18. In a combination according to claim 17, the improved apparatus wherein the third connecting means is fixedly secured to the bar.

19. In a combination according to claim 14, the improved apparatus wherein the third connecting means includes a dovetail connector to secure the bar to the lifting arm, said dovetail connector being releasable in response to force in a direction opposite to the direction of lifting force.

20. An apparatus for use in a surgical procedure to connect a first retractor and a second retractor each including a connector half of a first type to a mechanical lifting arm including a connector half of a second type to raise a tissue plane of the body, the retractors requiring application of a lifting force and a lifting torque to lift the tissue plane, the lifting torque being applied about an axis generally perpendicular to the lifting force, part of the retractors being inserted into the body, internal of the epidermis, to transmit the lifting force, the apparatus comprising:

a bar, having a center, the bar being elongate and defining a longitudinal axis;

a first connecting means including a connector half of the second type capable of mating with the connector half of the first type of the first retractor, slidably mounted on the bar and lockable to the bar, for detachably and rigidly connecting the first retractor to the bar, the first connecting means transmitting the lifting force and the lifting torque from the bar to the first retractor and generally preventing the first retractor from moving relative to the bar;

a second connecting means including a connector half of the second type capable of mating with the connector half of the first type of the second retractor, slidably mounted on the bar and lockable to the bar, for detachably and rigidly connecting the second retractor to the bar, the second connecting means transmitting the lifting force and the lifting torque from the bar to the second retractor and generally preventing the second retractor from moving relative to the bar;

a third connecting means, attached to the center of the bar including a connector half of the first type capable of mating with the connector half of the second type of the mechanical lifting arm, for detachably and rigidly connecting the bar to the mechanical lifting arm, the third connecting means transmitting the lifting force and the lifting torque from the mechanical lifting arm to the bar, and generally preventing the bar from moving relative to the mechanical lifting arm; and wherein the connector half of the first type and the connector half of the second type together constitute a dovetail connector.

21. The apparatus of claim 20 wherein the connector half of the first type is a male half of a dovetail connector, and the connector half of the second type of connector is a female half of a dovetail connector.

* * * * *